(12) United States Patent
Hu et al.

(10) Patent No.: US 8,198,254 B2
(45) Date of Patent: Jun. 12, 2012

(54) ANNEXIN A9 (ANXA9) BIOMARKER AND THERAPEUTIC TARGET IN EPITHELIAL CANCER

(75) Inventors: Zhi Hu, El Cerrito, CA (US); Wen-Lin Kuo, San Ramon, CA (US); Richard M. Neve, San Mateo, CA (US); Joe W. Gray, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/412,304

(22) Filed: Mar. 26, 2009

(65) Prior Publication Data

US 2009/0318533 A1 Dec. 24, 2009

Related U.S. Application Data

(60) Provisional application No. 61/040,117, filed on Mar. 27, 2008.

(51) Int. Cl.
*A61K 48/00* (2006.01)
*C07H 21/02* (2006.01)
*C07H 21/04* (2006.01)

(52) U.S. Cl. .................... 514/44; 536/23.1; 536/24.5

(58) Field of Classification Search .................. None
See application file for complete search history.

(56) References Cited

U.S. PATENT DOCUMENTS 6,268,184 B1  7/2001  Gray et al.

OTHER PUBLICATIONS

Wall, N.R. et al, "Small RNA: can RNA interference be exploited for therapy", Lancet 2003; 362: 1401-03.
Scanlon, K.J., "Anti-Genes: siRNA, Ribozymes and Antisense", Curr Pharm Biotech 2004; 4: 415-420.
Buckingham, S.D., "RNA interference: from model organisms towards therapy for neural and neuralmuscular disorders", Human Molecular Genetics 2004, vol. 13, Review Issue 2: R275-R288.
Liao, Y. et al, "Enhanced paclitaxel cytotoxicity and prolonged animal survival rate by a nonviral-mediated systemic delivery of E1A gene in orthotopic xenograft human breast cancer", Cancer Gene Therapy 2004; 11: 594-602.
Yano, J. et al, "Antitumor Activity of Small Interfering RNA/Cationic Liposome Complex in Mouse Models of Cancer", Clinical Cancer Research 2004, vol. 10: 7721-7726.
Zhao, N. et al, "Knockdown of Mouse Adult Beta-Globin Gene Expression in MEL Cells by Retrovirus Vector-Mediated RNA Interference", Molecular Biotechnology 2004; vol. 28: 195-200.
Sumimoto, H. et al, "Gene therapy for human small-cell lung carcinoma by inactivation of Skp-2 with virally mediated RNA interference", Gene Therapy 2005; vol. 12: 95-100.
Schiffelers, R.M. et al, "Cancer siRNA therapy by tumor selective delivery with ligand-targeted sterically stabilized nanoparticle", Nucleic Acids Research 2004, vol. 32, No. 19: e149.
Walker-Daniels, J. et al, "Differential Regulaton of EphA2 in Normal and Malignant Cells", Am J Path 2003; vol. 162: 1037-1042.

Kinch, M.S. et al., "Overexpression and functional alterations of the EphA2 tyrosine kinase in cancer", Clinical & Experimental Metastasis 2003; 20: 59-68.
Thaker, P.H. et al, "EphA2 Expression Is Associated with Aggressive Features in Ovarian Carcinoma", Clinical Cancer Research 2004, vol. 10: 5145-5150.
Albertson, D.G. et al, "Chromosome aberrations in solid tumors", Nature Genetics 2003; vol. 34, No. 4: 369-376.
Knuutila, S., in "Correspondence", "Online Access to CGH Data of DNA Sequence Copy Number Changes", Am J Path 2000; vol. 157, No. 2: 689.
Baylin, S.B. et al, "DNA hypermethylation in tumorigenesis: epigenetics joins genetics", Trends in Genetics 2000; vol. 16, No. 4: 168-174.
Jones, P.A., "Overview of Cancer Epigenetics", Seminars in Hematology 2005; S3-58.
Hanahan, D. et al, "The Hallmarks of Cancer", Cell 2000; vol. 100: 57-70.
Perou, C.M. et al, "Distinctive gene expression patterns in human mammary epithelial cells and breast cancers", Proc. Natl Acad. Sci. USA 1999; vol. 96: 9212-9217.
Perou, C.M. et al, "Molecular portraits of human breast cancers", Nature 2000; vol. 406: 747-752.
Sorlie, T. et al, "Gene expression patterns of breast carcinomas distinguish tumor subclasses with clinical implications", PNAS 2001; vol. 98, No. 9: 10869-10874.
Sorlie, T. et al, "Repeated observation of breast tumor subtypes in independent gene expression data sets", PNAS 2003; vol. 100, No. 4: 8418-8423.
Ramaswamy, S. et al, "A molecular signature of metastasis in primary solid tumors", Nature Genetics 2003; vol. 33: 49-54.
Esteva, F.J. et al, "Prognostic Role of a Multigene Reverse Transcriptase-PCR Assay in Patients with Node-Negative Breast Cancer Not Receiving Adjuvant Systemic Therapy", Clin Cancer Res 2005; 11 (9): 3315-3319.
Gianni, L. et al, "Gene Expression Profiles in Paraffin-Embedded Core Biopsy Tissue Predict Response to Chemotherapy in Women with Locally Advanced Breast Cancer", J Clin Oncol 2005; 23: 7265-7277.
Van 'T Veer, L.J. et al, "Gene expression profiling predicts clinical outcome of breast cancer", Nature 2002; vol. 415: 530-536.
Al-Kuraya, K. et al, "Prognostic Relevance of Gene Amplifications and Coamplifications in Breast Cancer", Cancer Research 2004; 64: 8534-8540.
Kallioniemi, A. et al, "Detection and mapping of amplified DNA sequences in breast cancer by comparative genomic hybridization", PNAS USA 1994; vol. 91: 2156-2160.
Kallioniemi, A. et al, "ERBB2 amplification in breast cancer analyzed by fluorescence in situ hybridization", PNAS USA 1992; vol. 89: 5321-5325.
Press, M.F. et al, "Diagnostic Evaluation of HER-2 as a Molecular Target: An Assessment of Accuracy and Reproducibility of Laboratory Testing in Large, Prospective, Randomized Clinical Trials", Clin Cancer Res 2005; 11 (18): 6598-6607.

(Continued)

*Primary Examiner* — Amy Bowman
(74) *Attorney, Agent, or Firm* — Michelle Chew Wong; Lawrence Berkeley Nat'l. Laboratory

(57) ABSTRACT

Amplification of the ANXA9 gene in human chromosomal region 1q21 in epithelial cancers indicates a likelihood of both in vivo drug resistance and metastasis, and serves as a biomarker indicating these aspects of the disease. ANXA9 can also serve as a therapeutic target. Interfering RNAs (iRNAs) (such as siRNA and miRNA) and shRNA adapted to inhibit ANXA9 expression, when formulated in a therapeutic composition, and delivered to cells of the tumor, function to treat the epithelial cancer.

5 Claims, 12 Drawing Sheets

OTHER PUBLICATIONS

Tanner, M.M. et al, "Increased Copy Number at 20q13 in Breast Cancer: Defining the Critical Region and Exclusion of Candidate Genes", Cancer Research 1994; 54: 4257-4260.

Loo, L.W.M. et al, "Array Comparative Genomic Hybridization Analysis of Genomic Alterations in Breast Cancer Subtypes", Cancer Research 2004; 64: 8541-8549.

Naylor, T.L. et al, "High resolution genomic anlayiss of sporadic breast cancer using array-based comparative genomic hybridization", Breast Cancer Research 2005, 7: R1186-R1198.

Pollack, J.R. et al, "Genome-wide analysis of DNA copy-number changes using cNDA microarrays", Nature Genetics 1999; 23: 41-46.

Pollack, J.R. et al, "Microarray analysis reveals a major direct role of DNA copy number alteration in the transcriptional program of human breast tumors", PNAS 2002; 99 (20): 12963-12968.

Volik, S. et al, "End-sequence profiling: Sequence-based analysis of aberrant genomes", PNAS 2003; 100 (13): 7696-7701.

Anand, N. et al, "Gene encoding protein elongation factor EEF1A2 is a putative oncogene in ovarian cancer", Nature Genetics 2002; 31: 301-305.

Gray, J.W. et al, "Specific Keynote: Genome Copy Number Abnormalities in Ovarian Cancer", Gynecologic Oncology 2003; 88: S16-S21.

Cheng, K.W. et al, "The RAB25 small GTPase determines aggressiveness of ovarian and breast cancers", Nature Medicine 2004; 10 (11): 1251-1256.

Lapuk, A. et al, "Computational BAC Clone Contig Assembly for Comprehensive Genome Analysis", Genes, Chromosomes & Cancer 2004; 40: 66-71.

Isola, J.J. et al, "Genetic Aberrations Detected by Comparative Genomic Hybridization Predict Outcome in Node-Negative Breast Cancer", Am J Path 1995; 147 (4): 905-911).

Jain, A.N. et al, "Quantitative analysis of chromosomal GCH in human breast tumors associates copy number abnormalities with p53 status and patient survival", PNAS 2001; 98 (14): 7952-7957.

Barlund, M. et al, "Multiple Genes at 17q23 Undergo Amplification and Overexpression in Breast Cancer", Cancer Research 2000; 60: 5340-5344.

Ray, M.E., et al, "Genomic and Expression Analysis of the 8p11-12 Amplicon in Human Breast Cancer Cell Lines", Cancer Research 2004; 64: 40-47.

Yi, Y. et al., "Coupled analysis of gene expression and chromosomal location", Genomics 2005; 85: 401-412.

Kauraniemi, P. et al, "New Amplified and Highly Expressed Genes Discovered in the ERBB2 Amplicon in Breast Cancer by cDNA Microarrays", Cancer Research 2001; 61: 8235-8240.

Kauraniemi, P. et al, "Amplification of a 280-Kilobase Core Region at the ERBB2 Locus Leads to Activiation of Two Hypothetical Proteins in Breast Cancer", Am J Path 2003; 163 (5): 1979-1984.

Gelsi-Boyer, V. et al, "Comprehensive Profiling of 8p11-12 Amplification in Breast Cancer", Mol Cancer Res 2005; 3 (12): 655-667.

FIG.3: Annexin A9 (ANXA9)

➢ mRNA:14 exons, Protein: 38.3kDa, 40% similarity to ANXA2
➢ Contains 4 atypical Annexin repeats, Ca2+ and phospholipid binding protein, a unique annexin member
➢ structural analysis suggested that 4 repeats of ANXA9 may form a calcium channel and so may be involved in transport of Ca2+, Cl-

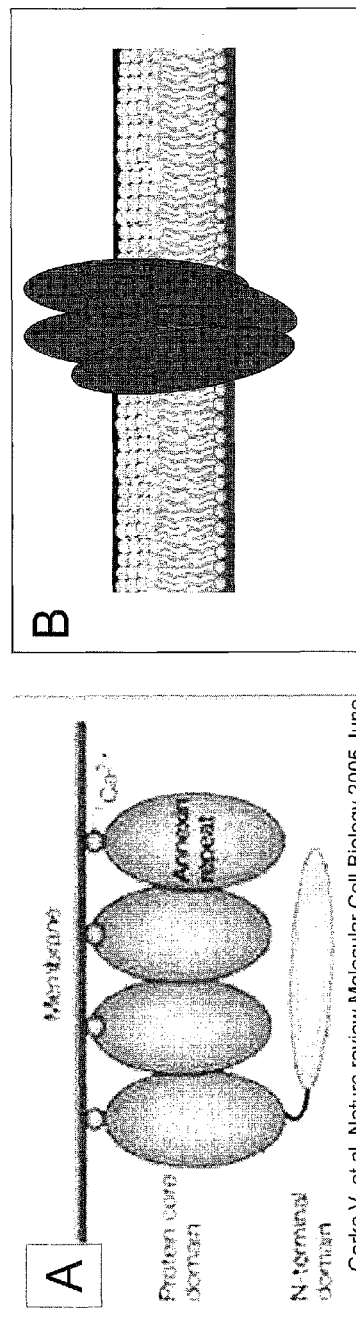

Two potential interaction types of annexin: A: attaching to the surface of membrane and B: insertion into membrane

FIG.11
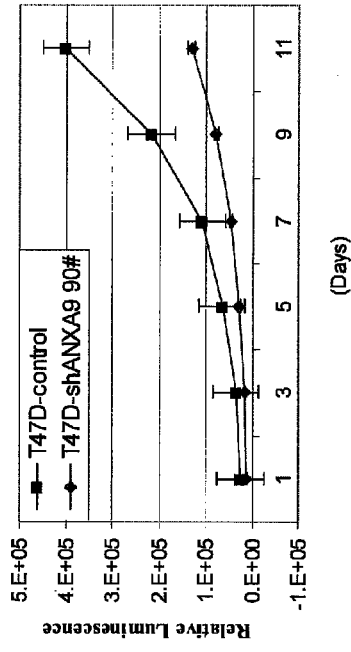
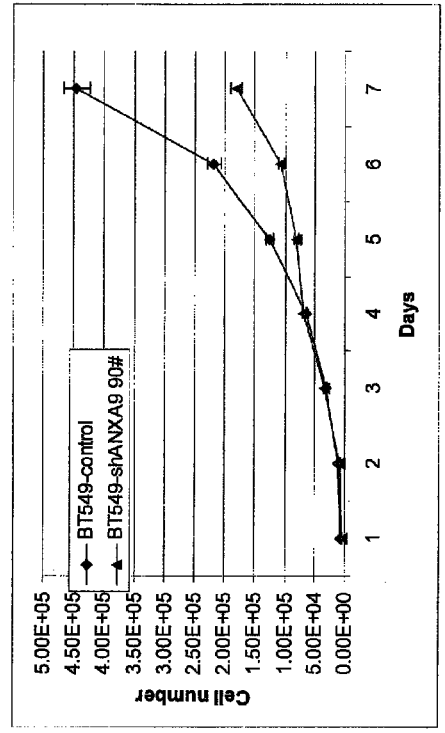
Cell growth curve
(cells selected by puromycin 5μg/ml)
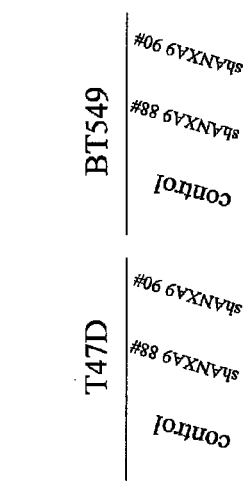
Detection of ANXA9 levels by western blot

FIG.12

1. To elucidate the molecular biology role of ANXA9 in the development of breast cancer Pathway may be involved in
   Cell cycle pathway
   PDGF pathway 2. To establish *In vivo* model to evaluate its clinical potential and biological importance in breast cancer

*In vivo* siRNA delivery model ?
   Transgenic RNAi model ?

| Gene Symbol | fold(up) | Gene Symbol | fold(down) |
|---|---|---|---|
| ANXA9 | 152 | RSAD2 | 36 |
| REG1A | 150 | OAS1 | 32 |
| CRISP3 | 35 | TRIM22 | 29 |
| NEB | 11 | IFIT1 | 27 |
| SERPINA3 | 11 | MX1 | 27 |
| PTGDS | 8 | OAS2 | 23 |
| USH1C | 8 | LAMP3 | 19 |
| LRRC17 | 7 | ID2 | 17 |
| RPL31 | 7 | IFIT3 | 17 |
| FABP7 | 6 | KRT15 | 17 |
| BGN | 6 | HERC6 | 16 |
| RNASE4 | 5 | DDX58 | 15 |
| SPON1 | 5 | G1P3 | 15 |
| GCN20 | 5 | PSMB9 | 14 |
| PTGDS | 5 | OAS3 | 13 |
| ANG | 5 | VGLL1 | 13 |
| GAS7 | 5 | STAT1 | 12 |
| IL2RA | 4 | GBP1 | 12 |
| TOX | 4 | G1P2 | 11 |
| CRTAP | 4 | ANXA1 | 10 |

Top 20 up or down regulated genes when HCC1569 cell overexpression of ANXA9

ANNEXIN A9 (ANXA9) BIOMARKER AND THERAPEUTIC TARGET IN EPITHELIAL CANCER

CROSS REFERENCE TO RELATED APPLICATIONS

This application claims benefit of and priority to U.S. Ser. No. 61/040,117 filed Mar. 27, 2008, which application is incorporated by reference in its entirety for all purposes.

STATEMENT OF GOVERNMENTAL SUPPORT

This invention was made during work supported by the National Cancer Institute, through Grants CA 58207 and CA 64602 and during work supported by the U.S. Department of Energy under Contract No. DE-AC02-05CH11231. The government has certain rights in this invention.

REFERENCE TO SEQUENCE LISTING AND TABLE APPENDIX

The present application incorporates the attached sequence listing in its entirety. The sequence listing in paper and computer readable form are identical.

FIELD OF THE INVENTION

The present invention relates to biomarkers for cancer that also serve as targets for therapeutic agents to treat the patient.

BACKGROUND OF THE INVENTION

Despite the research and effort of many scientists and practioners throughout the world, cancer remains a deadly disease, challenging the entire population. Epithelial cancers including breast, lung, ovary, bladder, head and neck, colon, and a host of other cancers originating in the epithelial layers of the local tissue represent 90% of all cancers, and manifest in the progression of solid tumor growth from a local primary site to metastasis all over the body. Drug therapies for epithelial cancers work for some patients and not for others, and until recently, the medical community could do little to predict which patients would be the likely non-responders.

The present invention, overcomes these challenges, as shall be disclosed and described herein.

BRIEF SUMMARY OF THE INVENTION

The present invention provides for the identification of a high priority apoptosis-suppressing gene, Annexin A9 (ANXA9) by identification of aberrations involving genome sequence, copy number and/or gene expression that are associated with increased tumor proliferation and apoptosis suppression. The marker for this gene can be developed to detect diseases characterized by increased expression of apoptosis-suppressing genes, such as aggressive cancers. Inhibitors of this gene can be developed to treat these diseases.

In one aspect, ANXA9 gene amplification at chromosomal location 1q21 is shown by the results described herein to be a useful marker for prediction and early detection of breast cancer. These data suggest that amplification at this location will also identify a poorly performing subset of patients that can be offered alternative therapies. Moreover, si/shRNA and/or small molecule inhibitors can be made for genes in regions of amplification at 1q21 that cause reduced apoptotic surveillance when over expressed. Inhibitors of this anti-apoptotic gene will likely be effective against tumors in which the target gene is amplified.

ANXA9 increases in copy number and is strongly over expressed in primary epithelial cancers, as evidenced by exemplary experiments in breast cancer. Silencing of ANXA9 inhibits cell growth/proliferation and induces cell apoptosis in cell lines where it is over expressed. Over expression of ANXA9 increases cell growth in cell lines where it is down regulated. ANXA9 is implicated in proliferative aspects of breast cancer pathophysiology and therefore development of a therapeutic target to ANXA9 is indicated.

Assays to predict metastatic potential in a lymph-node negative cancer patient include identifying an apparently non-metastatic cancerous tumor in the patient, determining that a lymph node of the patient is essentially negative for the tumor cells in a standard lymph node biopsy, and detecting ANXA9 expression in cells from a biopsy of the tumor. Detection of ANXA9 expression indicates that the cells are more likely to become metastatic compared to tumor cells not expressing ANXA9. The assay can be applied with particular usefulness to epithelial tumors in humans.

BRIEF DESCRIPTION OF THE DRAWINGS

FIG. 3 shows cartoons of Annexin proteins which may have 2 possible states in cells. A shows that annexin may attach to the cell surface via the interaction of Calcium and membrane. B shows that Annexin may insert into the membrane and extend to outside. Thus, ANXA9 may be a logical drug target according to its structure.

FIG. 11 shows inhibition of cell growth by expression of shANXA9. The lenti virus shRNA clones of ANXA9 were stably transfected into T47D and BT549 cells. Western Blot data showed that one of clone can completely knock down expression of ANXA9. The graph shows the cell growth curve; the pink curve is the cells with shRNA and the blue curve is the control cells. From the results it can be seen that the pink curve is much slower than the blue, thus cells with ANXA9 shRNA grow much slower than the control cells.

FIG. 12 is a partial screenshot of the array data as analyzed by Ingenuity System. The right panel shows a table of the top 20 up and down regulated genes associated with ANXA9 over expression. We identified differentially activated cell-signaling networks such as the cell cycle pathway, PDGF pathway which are associated with ANXA9 over expression.

DETAILED DESCRIPTION OF THE PREFERRED EMBODIMENT

A comprehensive analysis of gene copy number and gene expression analysis was applied in 146 primary breast tumors and 55 breast cancer cell lines. Amplified regions at chromosomes 1q21, 8p11, 11q13, 17q12 and 20q13 are associated with reduced survival duration of breast cancer patients. Genes located on these regions are interesting candidate targets for breast cancer.

Figure 1:
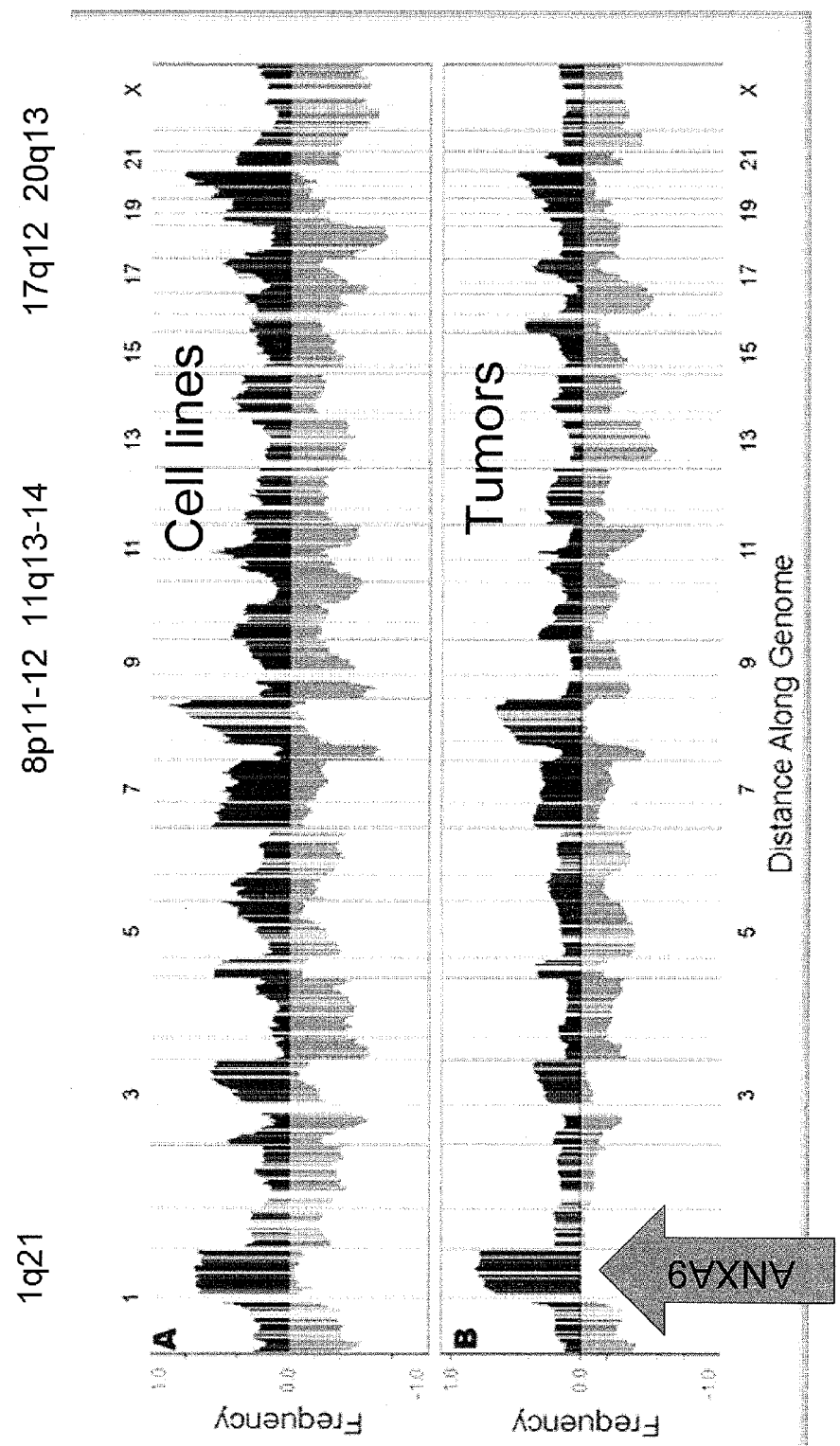
FIG. 1 is a graph showing recurrent aberrations in breast cancer detected using array CGH. Frequencies of chromosome aberrations (gains positive values, losses negative values) are displayed as a function of distance along the genome. Vertical lines show chromosome boundaries. Dashed vertical lines show centromere locations. The green arrow shows high level amplification of ANXA9 in cell lines and tumors. Panel A shows analyses of 55 breast cancer cell lines. Panel B show analyses of 146 primary breast cancer tumors.

One of the genes named Annexin A9 (ANXA9) located at chromosomal location 1q21.1-1q21.3 was found to be related to increased proliferation and suppressing apoptosis in breast cancer. (See FIG. 1). Until now there is little known of ANXA9 in breast cancer. For ANXA9, its mRNA includes 14 exons. The closest family member is ANXA2 and they have 40% similarity. It contains 4 Annexin repeats, $Ca^{2+}$ and phospholipid binding protein, but it mutated in the annexin repeats and this is unusual in annexins. Thus, ANXA9 is a unique annexin member. (See FIG. 3). (149,221,123 bp from pter-End:, 149,234,738 bp from pterSize)

The annexins are a family of calcium-dependent phospholipid-binding proteins. Members of the annexin family contain 4 internal repeat domains, each of which includes a type II calcium-binding site. The calcium-binding sites are required for annexins to aggregate and cooperatively bind anionic phospholipids and extracellular matrix proteins. This gene encodes a divergent member of the annexin protein family in which all four homologous type II calcium-binding sites in the conserved tetrad core contain amino acid substitutions that ablate their function. However, structural analysis suggests that the conserved putative ion channel formed by the tetrad core is intact.

ANXA9 as a Molecular Marker

Figure 2:
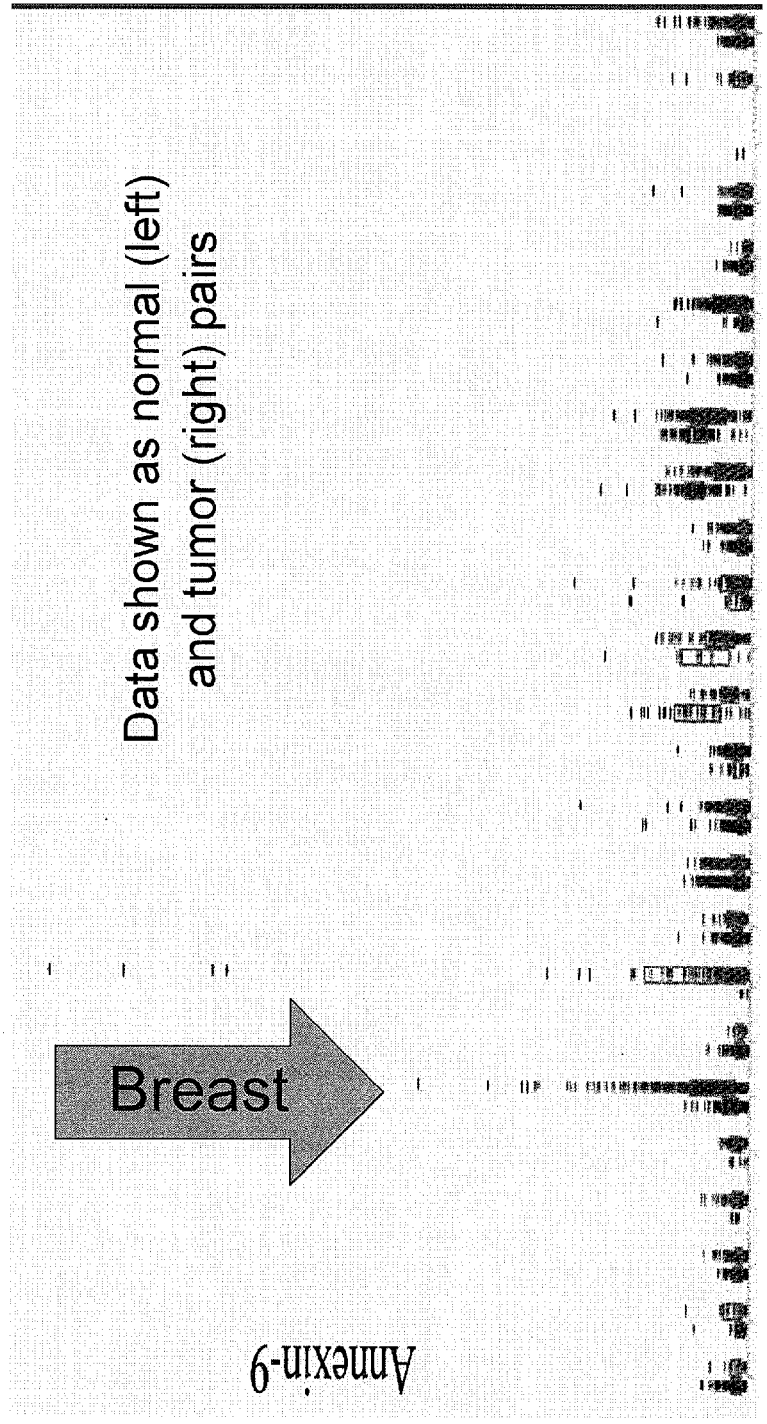
FIG. 2 shows the expression data of ANXA9 levels in different types of human tissues and paired tumors samples. For each type, Left are normal tissues and right are tumor pairs. Each spot stands for individual case. From the results, ANXA9 has relative low expression in normal tissues. ANXA9 highly up-regulated in breast cancers comparing to other cancer types and normal tissues
Figure 4:
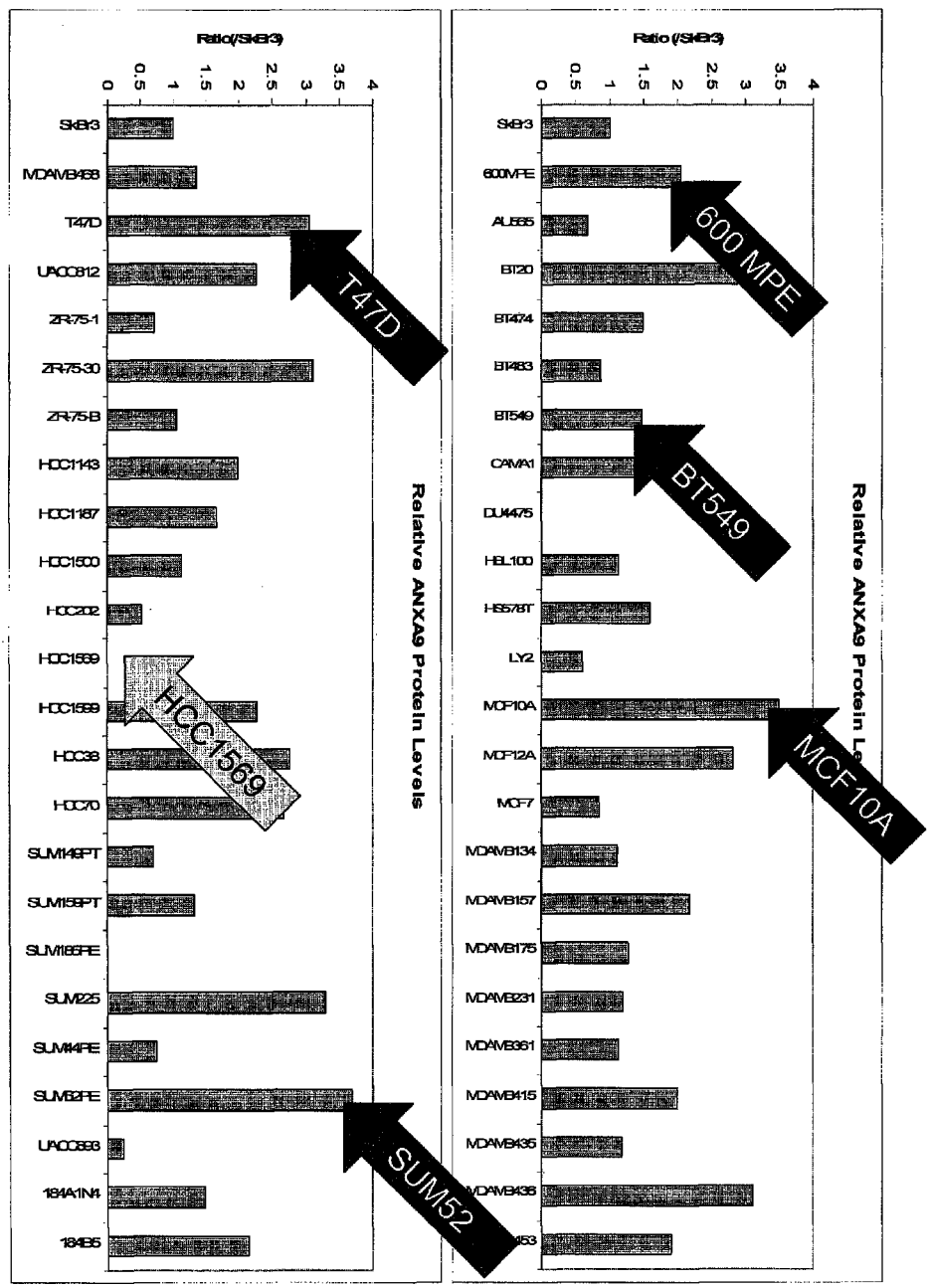
FIG. 4 are bar graphs showing protein levels of ANXA9 as measured in breast cancer cell lines by western blot and SkBr3 cell line as internal control. ANXA9 was then functionally assessed in cell lines wherein the protein levels were strongly up and down regulated.
Figure 5:
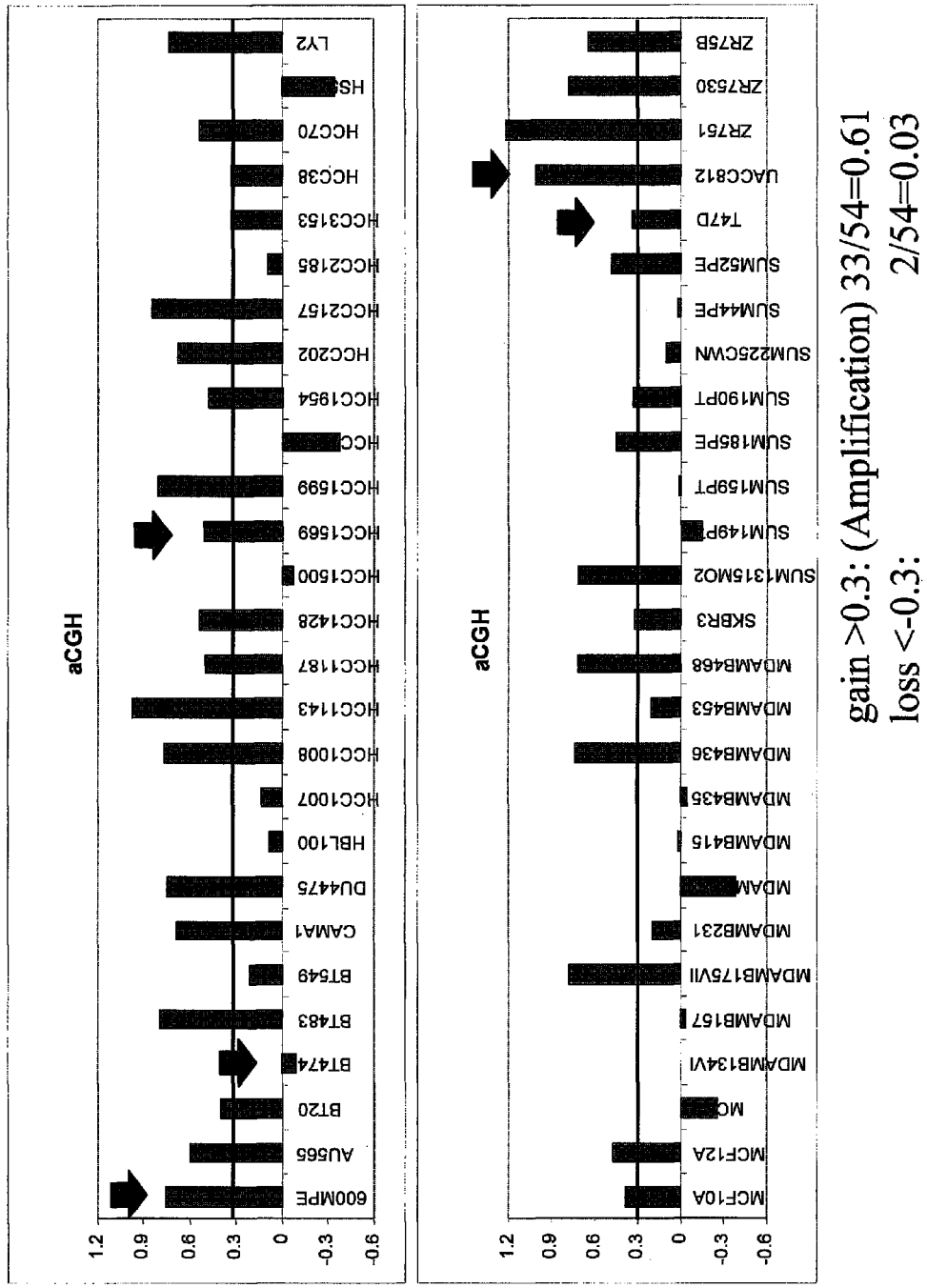
FIG. 5 are bar graphs of array CGH data of ANXA9 gene in 54 breast cancer cell lines. The copy number of ANXA9 gene was amplified in more than 60% of cell lines such as 600MPE, MCF10A, T47D, UACC812.
Figure 6:
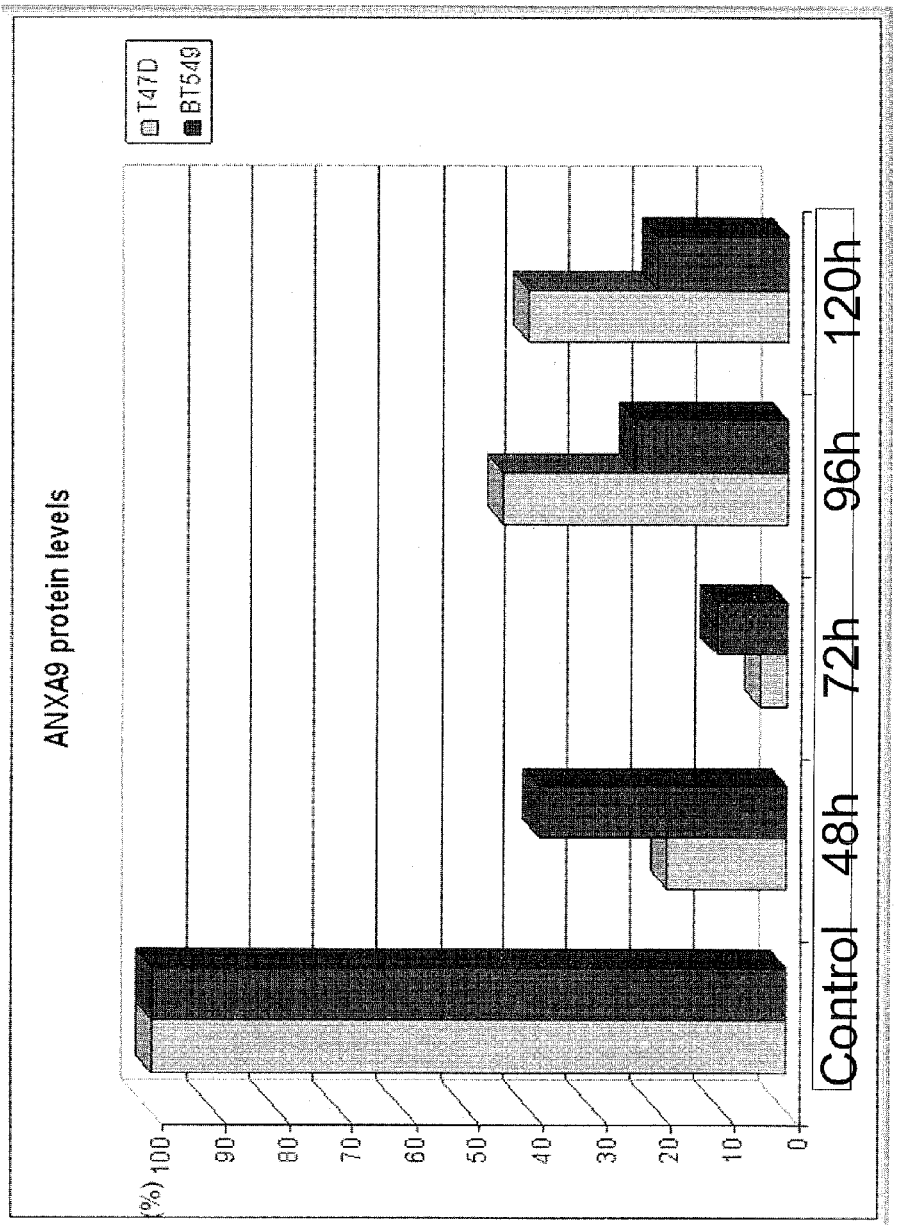
FIG. 6 is a bar graph showing the level of detection of ANXA9 in cells after treatment with ANXA9 siRNA pool and non specific siRNA as negative control at different time points. This figure shows relative protein levels of ANXA9 were reduced by 48 hr compared to the control cells after treated cell with siRNA. More than 90% of ANXA9 was knocked down by 72 hours.
Figure 7:
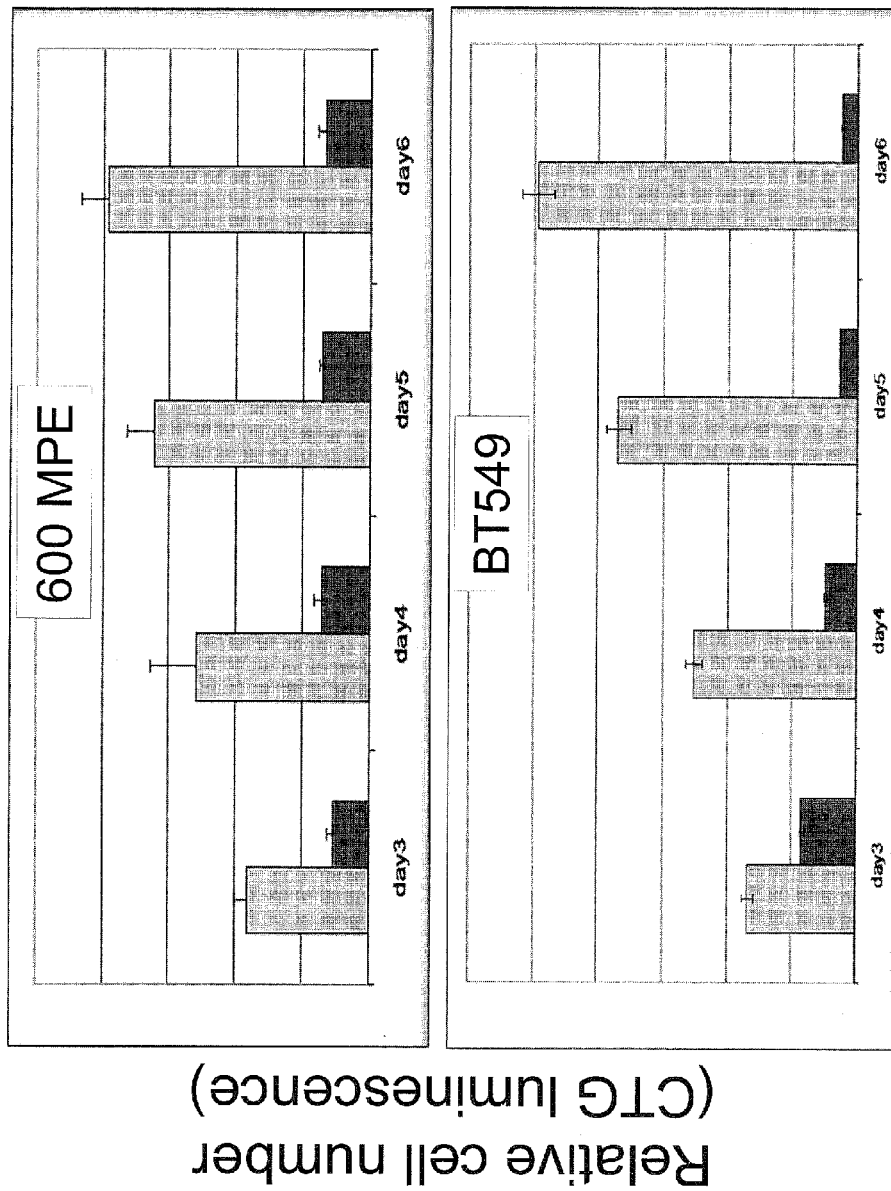
FIG. 7 are two bar graphs showing ANXA9 siRNA strongly inhibited growth in cell lines in which ANXA9 was over expressed as detected using a cell luminescence assay.

The identification of ANXA9 genome sequence, copy number and/or gene expression was associated with reduced survival duration in serous breast cancer and may be associated with reduced survival in certain diseases, such as cancers in tissues including but not limited to breast, ovary, bladder, head and neck, and colon, and epithelial cancers, such as ovarian, cervical, endometrium, lung, prostate and specifically breast cancer. ANXA9 shows relatively low expression in normal tissues as compared with tumor samples, see FIG. 2. Therefore, in some embodiments, ANXA9 can be used as a predictive marker or serum marker for breast cancer detection. Assessment of amplification at 1q21 can be readily detected by methods known in the art. In another embodiment, a prognostic method for predicting the outcome of a patient by detection of ANXA9 over expression in a patient tissue or biopsy. Thus, detection of increased expression of ANXA9 indicates the presence of aggressive cancers, i.e., the presence of cells in the tissue that will increase tumor progression and metastasize to other tissues.

Fluorescent In Situ Hybridization

In one embodiment, the amplification at 1q21 can be detected using multi-color Fluorescent In Situ Hybridization (FISH) methods. This is important from a translational point of view since FISH can be readily applied to paraffin embedded samples and paths to FDA approval of FISH based assays are well established (see Sokolova, I. A. et al. The development of a multitarget, multicolor fluorescence in situ hybridization assay for the detection of urothelial carcinoma in urine. *J Mol Diagn* 2, 116-23 (2000)). To this end, in one embodiment, the invention provides for a fully validated FISH assay as a predictive marker for early breast cancer.

In one embodiment, elevated gene expression is detected using FISH to detect 1q21 amplification. For example, one can create probes that hybridize to the 1q21 region, found in GenBank Accession No: NM_003568, which correlates to the mRNA of ANXA9 and is hereby incorporated by reference. Probes can be created by methods known in the art based upon the sequences of genes in 1q21. DNA from the probe generated can be produced and labeled with known fluorescent dyes, such as Spectrum Orange, Spectrum Green and Spectrum Aqua (Vysis, Inc.) to produce hybridization probes for detection of amplification at the test loci. In a preferred embodiment, probe production and labeling will be accomplished using Good Manufacturing Practices (GMP) at Vysis so that the analyses will be useful in obtaining FDA approval for clinical use of these markers. In another embodiment, the in situ hybridization methods of identifying probes described in U.S. Pat. No. 6,268,184, which is hereby incorporated by reference, is used. Methods of preparing probes are well known to those of skill in the art (see, e.g. Sambrook et al., Molecular Cloning: A Laboratory Manual (2nd ed:), Vols. 1-3, Cold Spring Harbor Laboratory, (1989) or Current Protocols in Molecular Biology, F. Ausubel et al., ed. Greene Publishing and Wiley-Interscience, New York (1987)).

In another embodiment, elevated expression is detected using FISH to detect chromosomal amplification. Probes can be created by methods described above based upon the genomic sequence containing and flanking genes in contigs covering Homo sapiens chromosome, 1q21, found at GenBank Accession Nos. NM_003568.

In another embodiment, a tri-locus fluorescence in situ hybridization (FISH) assay can be used to detect high level amplification at three chromosomal regions, at least one of which is 1q21 for paraffin embedded samples that will identify patients that will survive less than 24 months with specificity >95% and sensitivity >60%. For the tri-locus FISH assay, three probes chosen from three different amplicons are chosen.

An example of a method that can be used to develop probes for the tri locus FISH assay is found in U.S. Pat. No. 6,268, 184, hereby incorporated by reference. The method as applied to development of probes for predicting the outcome of breast cancer can be as follows.

Methods of preparing probes are well known to those of skill in the art (see, e.g. Sambrook et al., Molecular Cloning: A Laboratory Manual (2nd ed.), Vols. 1-3, Cold Spring Harbor Laboratory, (1989) or Current Protocols in Molecular Biology, F. Ausubel et al., ed. Greene Publishing and Wiley-Interscience, New York (1987)), which are hereby incorporated by reference.

The probes are most easily prepared by combining and labeling one or more constructs. Prior to use, constructs are fragmented to provide smaller nucleic acid fragments that easily penetrate the cell and hybridize to the target nucleic acid. Fragmentation can be by any of a number of methods well known to hose of skill in the art. Preferred methods include treatment with a restriction enzyme to selectively cleave the molecules, or alternatively to briefly heat the nucleic acids in the presence of $Mg^{2+}$. Probes are preferably fragmented to an average fragment length ranging from about 50 bp to about 2000 bp, more preferably from about 100 bp to about 1000 bp and most preferably from about 150 bp to about 500 bp.

Labeling Probes. Methods of labeling nucleic acids are well known to those of skill in the art. Preferred labels are those that are suitable for use in in situ hybridization. The nucleic acid probes may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g., $^{32}P$, $^{125}I$, $^{14}C$, $^{3}H$, and $^{35}S$), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. DYNABEADS™), and the like. Examples of labels which are not directly detected but are detected through the use of directly detectable label include biotin and dioxigenin as well as haptens and proteins for which labeled antisera or monoclonal antibodies are available.

The particular label used is not critical to the present invention, so long as it does not interfere with the in situ hybridization of the stain. However, stains directly labeled with fluorescent labels (e.g. fluorescein-12-dUTP, Texas Red-5-dUTP, etc.) are preferred for chromosome hybridization.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectable in as low copy number as possible thereby maximizing the sensitivity of the assay and yet be detectible above any background signal. Finally, a label must be chosen that provides a highly localized signal thereby providing a high degree of spatial resolution when physically mapping the stain against the chromosome. Particularly preferred fluorescent labels include fluorescein-12-dUTP and Texas Red-5-dUTP.

The labels may be coupled to the probes in a variety of means known to those of skill in the art. In a preferred embodiment the nucleic acid probes will be labeled using nick translation or random primer extension (Rigby, et al. J. Mol. Biol., 113: 237 (1977) or Sambrook, et al., Molecular Cloning—A Laboratory Manual, Cold Spring Harbor Laboratory, Cold Spring Harbor, N.Y. (1985)).

One of skill in the art will appreciate that the probes of this invention need not be absolutely specific for the targeted 1q21 region of the genome. Rather, the probes are intended to produce "staining contrast". "Contrast" is quantified by the ratio of the probe intensity of the target region of the genome to that of the other portions of the genome. For example, a DNA library produced by cloning a particular chromosome (e.g. chromosome 7) can be used as a stain capable of staining the entire chromosome. The library contains both sequences found only on that chromosome, and sequences shared with other chromosomes. Roughly half the chromosomal DNA falls into each class. If hybridization of the whole library were capable of saturating all of the binding sites on the target chromosome, the target chromosome would be twice as bright (contrast ratio of 2) as the other chromosomes since it would contain signal from the both the specific and the shared sequences in the stain, whereas the other chromosomes would only be stained by the shared sequences. Thus, only a modest decrease in hybridization of the shared sequences in the stain would substantially enhance the contrast. Thus contaminating sequences which only hybridize to non-targeted sequences, for example, impurities in a library, can be tolerated in the stain to the extent that the sequences do not reduce the staining contrast below useful levels.

Detecting the 1q21 Amplicons

It is contemplated that detection of amplification in the 1q21 amplicon is indicative of the presence and/or prognosis of a large number of cancers. These include, but are not limited to breast, ovary, bladder, head and neck, and colon. It has been shown that detection of amplification in the 1q21 amplicon is at least indicative of poor outcome in breast cancer patients. Thus, detection of increased expression of ANXA9 indicates the presence of aggressive cancers, i.e., the presence of cells in the tissue that will increase tumor progression and metastasize to other tissues.

In some embodiments, 1q21 amplification is detected through the hybridization of a probe of this invention to a target nucleic acid (e.g. a chromosomal sample) in which it is desired to screen for the amplification. Suitable hybridization formats are well known to those of skill in the art and include, but are not limited to, variations of Southern Blots, in situ hybridization and quantitative amplification methods such as quantitative PCR (see, e.g. Sambrook, supra., Kallioniemi et al., Proc. Natl Acad Sci USA, 89: 5321-5325 (1992), and PCR Protocols, A Guide to Methods and Applications, Innis et al., Academic Press, Inc. N.Y., (1990)).

In situ Hybridization. In another embodiment, the 1q21 amplicon is identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. Proc. Natl. Acad. Sci. USA, 85: 9138-9142 (1988) and in EPO Pub. No. 430,402. Suitable hybridization protocols can also be found in Methods in Molecular Biology Vol. 33, In Situ Hybridization Protocols, K. H. A. Choo, ed., Humana Press, Totowa, N.J., (1994). In a particularly preferred embodiment, the hybridization protocol of Kallioniemi et al., ERBB2 amplification in breast cancer analyzed by fluorescence in situ hybridization. *Proc Natl Acad Sci USA,* 89: 5321-5325 (1992) is used.

Typically, it is desirable to use dual color FISH, in which two probes are utilized, each labeled by a different fluorescent dye. A test probe that hybridizes to the region of interest is labeled with one dye, and a control probe that hybridizes to a different region is labeled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., Cytogenet. Cell Genet. 60: 190-193 (1992)). For instance, small biopsy tissue samples from tumors can be used for touch preparations (see, e.g., Kallioniemi, A. et al., Cytogenet. Cell Genet. 60: 190-193 (1992)). Small numbers of cells obtained from aspiration biopsy or cells in bodily fluids (e.g., blood, urine, sputum and the like) can also be analyzed. For prenatal diagnosis, appropriate samples will include amniotic fluid and the like.

It is preferred that the assay is validated by application to a larger sample for validation in a retrospective analysis of paraffin embedded samples from 700 moderate and high risk breast cancers (60% five year survival), the majority treated with platinum based therapy and 500 high risk cancers treated with cisplatinum and taxane.

In another embodiment, the assay can be used to determine the efficacy of traditional, current and new treatment protocols.

Quantitative PCR

In another embodiment, elevated gene expression is detected using quantitative PCR. Primers can be created using the sequences of genes identified in the GenBank Accession genomic sequences for 1q21, to detect sequence amplification by signal amplification in gel electrophoresis. As is known in the art, primers or oligonucleotides are generally 15-40 bp in length, and usually flank unique sequence that can be amplified by methods such as polymerase chain reaction (PCR) or reverse transcriptase PCR (RT-PCR, also known as real-time PCR). Methods for RT-PCR and its optimization are known in the art. An example is the PROMEGA PCR Protocols and Guides, found at URL:<http://www-.promega.com/guides/pcr_guide/default.htm>, and hereby incorporated by reference. Currently at least four different chemistries, TaqMan® (Applied Biosystems, Foster City, Calif., USA), Molecular Beacons, Scorpions® and SYBR® Green (Molecular Probes), are available for real-time PCR. All of these chemistries allow detection of PCR products via the generation of a fluorescent signal. TaqMan probes, Molecular Beacons and Scorpions depend on Forster Resonance Energy Transfer (FRET) to generate the fluorescence signal via the coupling of a fluorogenic dye molecule and a quencher moiety to the same or different oligonucleotide substrates. SYBR Green is a fluorogenic dye that exhibits little fluorescence when in solution, but emits a strong fluorescent signal upon binding to double-stranded DNA.

Two strategies are commonly employed to quantify the results obtained by real-time RT-PCR; the standard curve method and the comparative threshold method. In this method, a standard curve is first constructed from an RNA of known concentration. This curve is then used as a reference standard for extrapolating quantitative information for mRNA targets of unknown concentrations. Another quantitation approach is termed the comparative $C_t$ method. This involves comparing the $C_t$ values of the samples of interest with a control or calibrator such as a non-treated sample or RNA from normal tissue. The $C_t$ values of both the calibrator and the samples of interest are normalized to an appropriate endogenous housekeeping gene.

In one embodiment, elevated gene expression is detected using an RT-PCR assay to detect transcription levels or detected using a PCR assay to detect amplification of at least one gene from each amplicon region, preferably ANXA9 (1q).

Immunochemical Assays

In some embodiments, elevated expression of ANXA9 is detected using an immunochemical assay to detect protein levels. Such immunochemical assays are known throughout the art and include Western blots and ELISAs.

In one embodiment, using known methods of antibody production, antibodies to ANXA9 are made. In some embodiments, elevated ANXA9 expression is detected using an immunochemical (IHC) assay to detect ANXA9 protein levels. Anti-ANXA9 specific antibodies can be made by general methods known in the art. A preferred method of generating these antibodies is by first synthesizing peptide fragments. These peptide fragments should likely cover unique coding regions in the candidate gene. Since synthesized peptides are not always immunogenic by their own, the peptides should be conjugated to a carrier protein before use. Appropriate carrier proteins include but are not limited to Keyhole limpet hemacyanin (KLH). The conjugated phospho peptides should then be mixed with adjuvant and injected into a mammal, preferably a rabbit through intradermal injection, to elicit an immunogenic response. Samples of serum can be collected and tested by ELISA assay to determine the titer of the antibodies and then harvested.

Polyclonal (e.g., anti-ANXA9) antibodies can be purified by passing the harvested antibodies through an affinity column. Monoclonal antibodies are preferred over polyclonal antibodies and can be generated according to standard methods known in the art of creating an immortal cell line which expresses the antibody.

Nonhuman antibodies are highly immunogenic in human and that limits their therapeutic potential. In order to reduce their immunogenicity, nonhuman antibodies need to be humanized for therapeutic application. Through the years, many researchers have developed different strategies to humanize the nonhuman antibodies. One such example is using "HuMAb-Mouse" technology available from MEDAREX, Inc. and disclosed by van de Winkel, in U.S. Pat. No. 6,111,166 and hereby incorporated by reference in its entirety. "HuMAb-Mouse" is a strain of transgenic mice which harbor the entire human immunoglobin (Ig) loci and thus can be used to produce fully human monoclonal antibodies such as monoclonal anti-ANXA9 antibodies.

In another embodiment, a prognostic method for predicting the outcome of a patient by detection of ANXA9 over expression in a patient tissue or biopsy using an immunohistochemical assay as compared to normal levels in a control sample. Presence of or over expression of ANXA9 detected can be used as an indicator of metastatic or invasive cells present in the patient tissue, which may likely lead to metastatic cancer in the near future. In another embodiment, over expression of ANXA9 can be determined by comparison to a reference expression level (such as the average expression level of the gene in a cell line panel or a cancer cell or tumor panel, or the like).

In another embodiment, a prognostic method to provide more accurate prognosis for patients having non-invasive cancer (e.g., lymph-node negative cancer) previously determined based on morphology by a pathologist. A new biopsy can be taken or biopsies previously taken and preserved (e.g., in paraffin) can be used. In addition to observing morphology of a tumor (e.g., histological grade, stage and size), detection of ANXA9 over expression can be carried out by IHC assay and a new prognosis determined, factoring in the finding of level of ANXA9 expression levels. For example, a finding by IHC that ANXA9 is present at an increased level as compared to a normal tissue, despite the morphology of a non-invasive cancer, will indicate that the tumor should be staged or graded higher as a tumor that will be invasive and aggressive, leading to metastasis.

Expression Profiling

In another embodiment, array comparative genomic hybridization (CGH) and expression profiling to localize aberrant genes in a patient is contemplated. Analysis of genome copy number abnormalities of ANXA9 using array CGH (Hodgson, G. et al. Genome scanning with array CGH delineates regional alterations in mouse islet carcinomas. *Nat Genet* 29, 459-64 (2001); Snijders, A. M. et al. Assembly of microarrays for genome-wide measurement of DNA copy number. *Nat Genet* 29, 263-4 (2001)) can be performed. In another embodiment, gene expression of ANXA9 is analyzed using an array such as the Affymetrix U133A array platform (Lancaster, J. M. et al. Gene expression patterns that characterize advanced stage serous ovarian cancers. *J Soc Gynecol Investig* 11, 51-9 (2004). In one embodiment, a finding of an increased expression profile of ANXA9 by about 1.5-fold is indicative of over expression and indicates early detection of breast cancer. In another embodiment, a finding of an increased expression profile of ANXA9 by about 1.5-fold is indicative of over expression and a prognosis of poor outcome in cancer.

Assay Kits

The present invention further provides kits for use within any of the above diagnostic methods. Such kits typically comprise two or more components necessary for performing a diagnostic assay. Components may be compounds, reagents, containers and/or equipment.

In one embodiment, one container within a kit may contain a set of FISH probes for detection of amplification at different loci, such as 1q21. One or more additional containers may enclose elements, such as reagents or buffers, to be used in the assay. Such kits may also, or alternatively, contain a detection reagent as described above that contains a reporter group suitable for direct or indirect detection of antibody binding.

In another embodiment, the kit may be comprised of a set of PCR primers to detect sequence amplification genes found in genomic sequences amplified in the 1q21. The kit would also contain such reagents as buffers, polymerase, Magnesium, or other elements necessary to carry out quantitative PCR.

ANXA9 as a Therapeutic Target

Prognostic markers that identify subsets of patients with very poor survival prospects are of modest clinical importance unless therapies can be developed for these patients. Our approach to therapy for these patients is to develop inhibitors of genes that are over expressed in the regions of amplification associated with reduced survival. It is contemplated that these candidate genes may be over expressed in diseases including but not limited, cancers, lymphomas, cardiovascular diseases, cardiac hypertrophy, and infectious diseases.

In one embodiment, genome wide analyses of genome copy number and gene expression in serous breast cancers showed that a region at chromosome 1q21 is amplified and over-expressed. Functional studies of ANXA9 and other genes in regions of recurrent abnormality in breast and other cancers are herein described. We consider ANXA9 to be high priority therapeutic targets in diseases wherein they are over expressed and associated with short survival rates.

ANXA9 is particularly important in the context of this application because they are at the site of recurrent high level amplification at 1q21 that is mostly strongly associated with short survival duration in breast and breast cancer. This gene was discovered by measuring gene expression levels using Affymetrix expression profiling and copy number levels using array CGH in ~80 breast cancers for which outcome information was available. Analyses of correlations between gene expression and genome copy number showed that over 1000 genes are deregulated by recurrent genome aberrations including several in the three regions of amplification associated with reduced survival duration.

Thus, herein is described complementary strategies to (a) develop and fully validate markers that identify patients with serous breast cancer that will survive less than 2 years under conventional treatment and (b) develop and evaluate therapies that will be preferentially effective in this group of patients and provide improved breast cancer management. Marker development is expected to be complete and fully validated within a short time and available commercially shortly thereafter. Prototypic therapies against ANXA9 and other outcome-associated genes will be developed as described and tested in preclinical models.

In some embodiments, ANXA9 is the candidate gene target for development of therapeutics and diagnostic assays. In one embodiment, an assay to detect elevated ANXA9 expression as a predictor of poor response to current drugs based therapies, such as taxol plus platinum based therapies, in serous breast cancers. In such an assay, elevated ANXA9 expression can be detected using methods known in the art or described above. It is contemplated that elevated ANXA9 expression can be detected in a subject by testing various tissues and bodily fluids, including but not limited to blood and serum. Thus, detection of elevated ANXA9 expression will indicate that the patient will likely respond poorly to current drug based therapies and is a candidate for use of other types of cancer therapies, combination therapies, and possibly require a therapeutic regimen usually reserved for later stage cancers.

In another embodiment, the detection of ANXA9 indicates that the patient should receive ANXA9-targeted therapeutics. We describe herein several types of therapeutics which can be used and further developed to target ANXA9.

Inhibitor Oligonucleotides and RNA interference (RNAi). The approaches to be taken will depend on the detailed characteristics of the genes, but in some embodiments, will begin with strategies to inhibit RNA transcription since they can, in principal, be used to attack over expressed genes independent of their biochemical composition. Work in the past two decades on transcriptional inhibitors focused on oligodeoxynucleotides and ribozymes. These approaches have had some clinical success but delivery issues limited their clinical utility. Recently, however, advances in short interfering RNA (siRNA) technology and biological understanding have accelerated development of anti-gene therapies (Wall, N. R. & Shi, Y. Small RNA: can RNA interference be exploited for therapy? *Lancet* 362, 1401-3 (2003); Scanlon, K. J. Antigenes: siRNA, ribozymes and antisense. *Curr Pharm Biotechnol* 5, 415-20 (2004); Buckingham, S. D., Esmaeili, B., Wood, M. & Sattelle, D. B. RNA interference: from model organisms towards therapy for neural and neuromuscular disorders. *Hum Mol Genet* 13 Spec No 2, R275-88 (2004)). Promising therapeutic approaches include siRNAs complexed with cationic liposomes (Liao, Y., et al., Enhanced paclitaxel cytotoxicity and prolonged animal survival rate by a nonviral-mediated systemic delivery of E1A gene in orthotopic xenograft human breast cancer. *Cancer Gene Ther* 11, 594-602 (2004); Yano, J. et al. Antitumor activity of small interfering RNA/cationic liposome complex in mouse models of cancer. *Clin Cancer Res* 10, 7721-6 (2004)), virus vector-mediated RNAi (Zhao, N. et al. Knockdown of Mouse Adult beta-Globin Gene Expression in MEL Cells by Retrovirus Vector-Mediated RNA Interference. *Mol Biotechnol* 28, 195-200 (2004); Sumimoto, H. et al. Gene therapy for human small-cell lung carcinoma by inactivation of Skp-2 with virally mediated RNA interference. *Gene Ther* (2004)) and nanoparticles adapted for siRNA (Schiffelers, R. M. et al. Cancer siRNA therapy by tumor selective delivery with ligand-targeted sterically stabilized nanoparticle. *Nucleic Acids Res* 32, e149 (2004)). In one embodiment, siRNAs against the high priority targets complexed with cationic liposomes and small molecule approaches to inhibit the over expressed candidate genes will allow rapid development of this line of attack.

In some embodiments, the expression of ANXA9 and other high priority apoptosis-associated genes is manipulated. In one embodiment, such manipulation can be made using optimized siRNAs. See Hannon, G. J. RNA interference (2002); Plasterk, R. H. in *Science* 1263-5 (2002); and Elbashir, S. M. et al. in *Nature* 494-8 (2001). Strong Pearson correlations between target gene amplification/expression levels and pro-apoptotic effects of siRNAs will indicate that copy number/expression levels determine the extent of apoptotic responses to target gene inhibitors. Spearman rank test correlations between amplification detected using the tri-locus test and the level of induced apoptosis will indicate that the FISH test predicts response to targeted therapeutics.

In another embodiment, treatment of amplified cells simultaneously with siRNAs against the apoptosis associated genes plus carboplatin or paclitaxel should result in the inhibition of apoptosis-associated amplicon genes and enhance patient response to carboplatin and paclitaxel. Greater than additive induction of apoptosis in these dual treatment experiments will indicate a synergistic effect. Studies can be conducted further to transfect cells that do not amplify/over express the target genes and determine whether over expression of the putative "anti-apoptotic" genes decreases sensitivity to carboplatin and/or paclitaxel.

The invention further provides for compounds to treat patients with elevated ANXA9 expression. In a preferred embodiment, the compound is an ANXA9 inhibitor such as, an antisense oligonucleotide; a siRNA oligonucleotide; a small molecule that interferes with ANXA9 function; a viral vector producing a nucleic acid sequence that inhibits ANXA9; or an aptamer.

High throughput methods can be used to identify ANXA9 inhibitors such as siRNA and/or small molecular inhibitor formulations to deliver ANXA9 (and other) inhibitors efficiently to cultured cells and xenografts. ANXA9 (and other) inhibitory formulations will be preferentially effective against xenografts that are amplified at the target loci and that these will enhance response to platinum and taxane compounds. Effective formulations using such methods as described above or in Example 2 will be developed for clinical application.

In some embodiments, known methods are used to identify sequences that inhibit ANXA9 and other candidate genes which are related to drug resistance and reduced survival rates. Such inhibitors may include but are not limited to, siRNA oligonucleotides, antisense oligonucleotides, peptide inhibitors and aptamer sequences that bind and act to inhibit ANXA9 expression and/or function.

In one embodiment, RNA interference is used to generate small double-stranded RNA (small interference RNA or siRNA) inhibitors to affect the expression of a candidate gene generally through cleaving and destroying its cognate RNA. Small interference RNA (siRNA) is typically 19-22 nt double-stranded RNA. siRNA can be obtained by chemical synthesis or by DNA-vector based RNAi technology. Using DNA vector based siRNA technology, a small DNA insert (about 70 bp) encoding a short hairpin RNA targeting the gene of interest is cloned into a commercially available vector. The insert-containing vector can be transfected into the cell, and expressing the short hairpin RNA. The hairpin RNA is rapidly processed by the cellular machinery into 19-22 nt double stranded RNA (siRNA). In a preferred embodiment, the siRNA is inserted into a suitable RNAi vector because siRNA made synthetically tends to be less stable and not as effective in transfection.

siRNA can be made using methods and algorithms such as those described by Wang L, Mu F Y. (2004) A Web-based Design Center for Vector-based siRNA and siRNA cassette. *Bioinformatics.* (In press); Khvorova A, Reynolds A, Jayasena S D. (2003) Functional siRNAs and miRNAs exhibit strand bias. *Cell.* 115(2):209-16; Harborth J, Elbashir S M, Vandenburgh K, Manninga H, Scaringe S A, Weber K, Tuschl T. (2003) Sequence, chemical, and structural variation of small interfering RNAs and short hairpin RNAs and the effect on mammalian gene silencing. *Antisense Nucleic Acid Drug Dev.* 13(2):83-105; Reynolds A, Leake D, Boese Q, Scaringe S, Marshall W S, Khvorova A. (2004) Rational siRNA design for RNA interference. *Nat Biotechnol.* 22(3): 326-30 and Ui-Tei K, Naito Y, Takahashi F, Haraguchi T, Ohki-Hamazaki H, Juni A, Ueda R, Saigo K. (2004) Guidelines for the selection of highly effective siRNA sequences for mammalian and chick RNA interference. *Nucleic Acids Res.* 32(3):936-48, which are hereby incorporated by reference.

Other tools for constructing siRNA sequences are web tools such as the siRNA Target Finder and Construct Builder available from GenScript (http://www.genscript.com), Oligo Design and Analysis Tools from Integrated DNA Technologies (URL:<http://www.idtdna.com/SciTools/SciTools.aspx>), or siDESIGN™ Center from Dharmacon, Inc. (URL:<http://design.dharmacon.com/default.aspx?source=0>). siRNA are suggested to be built using the ORF (open reading frame) as the target selecting region, preferably 50-100 nt downstream of the start codon. Because siRNAs function at the mRNA level, not at the protein level, to design an siRNA, the precise target mRNA nucleotide sequence may be required. Due to the degenerate nature of the genetic code and codon bias, it is difficult to accurately predict the correct nucleotide sequence from the peptide sequence. Additionally, since the function of siRNAs is to cleave mRNA sequences, it is important to use the mRNA nucleotide sequence and not the genomic sequence for siRNA design, although as noted in the Examples, the genomic sequence can be successfully used for siRNA design. However, designs using genomic information might inadvertently target introns and as a result the siRNA would not be functional for silencing the corresponding mRNA.

Rational siRNA design should also minimize off-target effects which often arise from partial complementarity of the sense or antisense strands to an unintended target. These effects are known to have a concentration dependence and one way to minimize off-target effects is often by reducing siRNA concentrations. Another way to minimize such off-target effects is to screen the siRNA for target specificity.

In one embodiment, the siRNA can be modified on the 5'-end of the sense strand to present compounds such as fluorescent dyes, chemical groups, or polar groups. Modification at the 5'-end of the antisense strand has been shown to interfere with siRNA silencing activity and therefore this position is not recommended for modification. Modifications at the other three termini have been shown to have minimal to no effect on silencing activity.

It is recommended that primers be designed to bracket one of the siRNA cleavage sites as this will help eliminate possible bias in the data (i.e., one of the primers should be upstream of the cleavage site, the other should be downstream of the cleavage site). Bias may be introduced into the experiment if the PCR amplifies either 5' or 3' of a cleavage site, in part because it is difficult to anticipate how long the cleaved mRNA product may persist prior to being degraded. If the amplified region contains the cleavage site, then no amplification can occur if the siRNA has performed its function.

In some embodiments, siRNA is designed based upon the mRNA sequence of ANXA, GenBank Accession No. NM_003568. In some embodiments, the siRNA are those found in Seq. ID No. 2-5, or similar thereto.

In another embodiment, antisense oligonucleotides ("oligos") can be designed to inhibit ANXA9 and other candidate gene function. Antisense oligonucleotides are short single-stranded nucleic acids, which function by selectively hybridizing to their target mRNA, thereby blocking translation. Translation is inhibited by either RNase H nuclease activity at the DNA:RNA duplex, or by inhibiting ribosome progression, thereby inhibiting protein synthesis. This results in discontinued synthesis and subsequent loss of function of the protein for which the target mRNA encodes.

In some embodiments, antisense oligos are phosphorothioated upon synthesis and purification, and are usually 18-22 bases in length. It is contemplated that the ANXA9 and other candidate gene antisense oligos may have other modifications such as 2'-O-Methyl RNA, methylphosphonates, chimeric oligos, modified bases and many others modifications, including fluorescent oligos.

In some embodiments, active antisense oligos should be compared against control oligos that have the same general chemistry, base composition, and length as the antisense oligo. These can include inverse sequences, scrambled sequences, and sense sequences. The inverse and scrambled are recommended because they have the same base composition, thus same molecular weight and Tm as the active antisense oligonucleotides. Rational antisense oligo design should consider, for example, that the antisense oligos do not anneal to an unintended mRNA or do not contain motifs known to invoke immunostimulatory responses such as four contiguous G residues, palindromes of 6 or more bases and CG motifs.

Antisense oligonucleotides can be used in vitro in most cell types with good results. However, some cell types require the use of transfection reagents to effect efficient transport into cellular interiors. It is recommended that optimization experiments be performed by using differing final oligonucleotide concentrations in the 1-5 µm range with in most cases the addition of transfection reagents. The window of opportunity, i.e., that concentration where you will obtain a reproducible antisense effect, may be quite narrow, where above that range you may experience confusing non-specific, non-antisense effects, and below that range you may not see any results at all. In a preferred embodiment, down regulation of the targeted mRNA (e.g. ANXA9 mRNA SEQ ID NO: 1) will be demonstrated by use of techniques such as northern blot, real-time PCR, cDNA/oligo array or western blot. The same endpoints can be made for in vivo experiments, while also assessing behavioral endpoints.

For cell culture, antisense oligonucleotides should be re-suspended in sterile nuclease-free water (the use of DEPC-treated water is not recommended). Antisense oligonucleotides can be purified, lyophilized, and ready for use upon re-suspension. Upon suspension, antisense oligonucleotide stock solutions may be frozen at −20° C. and stable for several weeks.

In another embodiment, aptamer sequences which bind to specific RNA or DNA sequences can be made. Aptamer sequences can be isolated through methods such as those disclosed in co-pending U.S. patent application Ser. No. 10/934,856, entitled, "Aptamers and Methods for their Invitro Selection and Uses Thereof," which is hereby incorporated by reference.

It is contemplated that the sequences described herein may be varied to result in substantially homologous sequences which retain the same function as the original. As used herein, a polynucleotide or fragment thereof is "substantially homologous" (or "substantially similar") to another if, when optimally aligned (with appropriate nucleotide insertions or deletions) with the other polynucleotide (or its complementary strand), using an alignment program such as BLASTN (Altschul, S. F., Gish, W., Miller, W., Myers, E. W. & Lipman, D. J. (1990) "Basic local alignment search tool." *J. Mol. Biol.* 215:403-410), and there is nucleotide sequence identity in at least about 80%, preferably at least about 90%, and more preferably at least about 95-98% of the nucleotide bases.

Antibody

It is further contemplated and would be well accepted by one with skill in the art that antibodies can be made to ANXA9 as described above. In one embodiment, a method of treatment using a humanized monoclonal ANXA9 antibody to down-regulate ANXA9.

In one embodiment, down regulation of ANXA9 at 1q21 and other high priority genes at 8p11, 8q24, 11q13 and 20q13 will be made using inhibitors preferentially toxic to cells detected as over amplified. It is contemplated that such down regulation will enhance response to platinum and taxane compounds because amplification at 1q21, 8q24, 11q13 and 20q13 increases resistance to carboplatin and/or pacitaxel.

In one embodiment, identifying genes that are over expressed in regions of amplification associated with reduced survival duration and for which inhibitors induce apoptosis in breast cancer cell lines in which the target is amplified is performed using ANXA9 as the prototype. However, levels of amplification and gene expression may vary substantially between serous breast cancers. These quantitative differences and the presence of other aberrations may influence the degree of response to amplicon gene targeted therapies.

High Throughput Screening. In one embodiment, high throughput screening (HTS) methods are used to identify compounds that inhibit ANXA9 and other candidate genes which are related to drug resistance and reduced survival rate, such as those amplified in the chromosomal 1q21, 8q24.1, 11q13.3 and 20q11-q13 regions. HTS methods involve providing a combinatorial chemical or peptide library containing a large number of potential therapeutic compounds (i.e., compounds that inhibit ANXA9 and other candidate genes which are related to drug resistance). Such "libraries" are then screened in one or more assays, as described herein, to identify those library members (particular peptides, chemical species or subclasses) that display the desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., ECIS TM, Applied Bio-Physics Inc., Troy, N.Y., MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Recombinant Expression

ANXA9 inhibitors such as the siRNA ANXA9 inhibitor described herein can also be expressed recombinantly. In general, the nucleic acid sequences encoding ANXA9 inhibitors such as the siRNA ANXA9 inhibitor and related nucleic acid sequence homologues can be cloned. This aspect of the invention relies on routine techniques in the field of recombinant genetics. Generally, the nomenclature and the laboratory procedures in recombinant DNA technology described herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 1994)).

ANXA9 and other candidate genes which are related to drug resistance and reduced survival rate are first cloned from cDNA and genomic DNA libraries or isolated using amplification techniques with oligonucleotide primers. Methods for making and screening cDNA libraries and genomic DNA libraries are well known (see, e.g., Gubler & Hoffman, Gene 25:263-269 (1983); Sambrook et al., supra; Ausubel et al., supra; Benton & Davis, *Science* 196:180-182 (1977); and Grunstein et al., *PNAS USA,* 72:3961-3965 (1975)).

Nucleic acids encoding sequences of candidate genes amplified in the chromosomal 1q21, 8q24.1, 11q13.3 and 20q13 regions and related to reduced survival rates, such as ANXA9 at 1q21 can also be isolated from expression libraries using antibodies as probes. Such polyclonal or monoclonal antibodies can be raised using methods known in the art (see, e.g., Harlow and Lane, Antibodies: A Laboratory Manual (1988)).

Substantially identical nucleic acids encoding sequences of candidate genes amplified in the chromosomal 1q21 can be isolated using nucleic acid probes and oligonucleotides under stringent hybridization conditions, by screening libraries.

Alternatively, expression libraries can be used to clone these sequences, by detecting expressed homologues immunologically with antisera or purified antibodies made against the core domain of nucleic acids encoding sequences of candidate genes amplified in the chromosomal 1q21 regions and related to reduced survival rates, such as ANXA9, which also recognize and selectively bind to the homologue.

Gene expression of candidate genes amplified in the chromosomal 1q21, 8q24.1, 11q13.3 and 20q13 regions and related to reduced survival rates, such as ANXA9 at 1q21, can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

To obtain high level expression of a cloned gene or nucleic acid sequence, such as those cDNAs encoding nucleic acid sequences encoding ANXA9 inhibitors such as the siRNA ANXA9 inhibitor and related nucleic acid sequence homologues, one typically subclones an inhibitor peptide sequence (e.g., nucleic acid sequences encoding ANXA9 inhibitors such as the siRNA ANXA9 inhibitor and related nucleic acid sequence homologue) into an expression vector that is subsequently transfected into a suitable host cell. The expression vector typically contains a strong promoter or a promoter/enhancer to direct transcription, a transcription/translation terminator, and for a nucleic acid encoding a protein, a ribosome binding site for translational initiation. The promoter is operably linked to the nucleic acid sequence encoding ANXA9 inhibitors such as the siRNA ANXA9 inhibitor or a subsequence thereof. Suitable bacterial promoters are well known in the art and described, e.g., in Sambrook et al. and Ausubel et al. The elements that are typically included in expression vectors also include a replicon that functions in a suitable host cell such as *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant ANXA9 inhibitors peptides to provide convenient methods of isolation, e.g., His tags. In some case, enzymatic cleavage sequences (e.g., Met-(His)g-Ile-Glu-GLy-Arg which form the Factor Xa cleavage site) are added to the recombinant ANXA9 inhibitor peptides. Bacterial expression systems for expressing the ANXA9 inhibitor peptides and nucleic acids are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

Standard transfection methods are used to produce cell lines that express large quantities of ANXA9 inhibitor, which can then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of cells is performed according to standard techniques (see, e.g., Morrison, J. Bact. 132:349-351 (1977); Clark-Curtiss & Curtiss, Methods in Enzymology 101:347-362 (Wu et al., eds, 1983). For example, any of the well known procedures for introducing foreign nucleotide sequences into host cells may be used. These include the use of calcium phosphate transfection, lipofectamine, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing ANXA9 inhibitor peptides and nucleic acids.

After the expression vector is introduced into the cells, the transfected cells are cultured under conditions favoring expression of ANXA9 inhibitors (e.g. siRNA or shRNA ANXA9 inhibitors) and related nucleic acid sequence homologues.

Other Options Using RNAi

RNAi is a naturally occurring gene regulatory mechanism, which has a number of advantages over other gene/antisense therapies including specificity of inhibition, potency, the small size of the molecules and the diminished risk of toxic effects, e.g., immune responses. Targeted, local delivery of RNAi to the lungs via inhalation offers in vivo delivery of siRNA or shRNA for the treatment of a range of diseases including cancer of the lungs, bronchea, esophagus, and other cancers within or tangential to or accessible from the airway path.

siRNA can be specifically synthesized and introduced into a cell to induce gene silencing. As this methodology exploits a naturally occurring pathway, it differs from other silencing technologies such as antisense oligonucleotides. In nature, RNAi is initiated when the cell encounters ectopic double stranded RNA (dsRNA), e.g., viral RNA, transposon or microRNA (miRNA). In the cytoplasm the RNase III-like protein dicer cleaves dsRNA from miRNAs or replicating viruses into siRNAs of 19-25 bases in length. The siRNA is then incorporated into the multiprotein RNA-induced silencing complex (RISC), which unwinds the duplex producing two strands; one strand (passenger) is discarded while the other (guide) can independently guide targeted mRNA recognition. The binding of siRNA results in a site-specific cleavage of the mRNA thereby silencing the message. The released cleavage products are degraded, and the siRNA: RISC complex is free to find another mRNA target. Degrading mRNA results in a profound reduction in the levels of the corresponding protein without altering the DNA. RNAi is therefore a highly promising therapeutic approach for diseases where aberrant protein production is a problem, such as cancers that over express ANXA9.

siRNA Design for ANXA9 Inhibition

Effective site selection algorithms and several siRNA design guides are currently available. The majority of in vivo siRNA experiments to date reported the use of 21-mer duplexes with a 19-base central double-stranded region and terminal 2-base 3' overhangs. This design mimics naturally occurring molecules produced by dicer processing in vivo. siRNA can be chemically synthesized or transcribed from a plasmid. In the case of the latter, a DNA insert of approximately 70 bp, encoding for a short hairpin RNA (shRNA) targeting the gene of interest, is cloned into a plasmid vector. The insert containing plasmid can then be transfected into a cell where the shRNA is expressed. The shRNA is rapidly processed by the cellular machinery into 19-22 nt siRNAs, which can then interfer with the expression of the target gene.

Several strategies are being explored to improve siRNA stability in vivo based on modifications previously used to improve the stability of antisense molecules. Commonly used modifications to improve stability include phosphorothioate (PS) or boranophosphate modification of the internucleoside linkage. Boranophosphate modifications confer significant nuclease resistance, but synthesis is complex, with modified bases being incorporated using in vitro transcription, making site-selective placement difficult. PS modifications are easier to position and will prolong the life of the siRNA when exposed to nucleases. It is important to note, however, that while limited PS modification preserves siRNA potency, over modification may decrease potency and/or increase toxicity.

A number of strategies can be used to prevent immune recognition and response, such as the use of delivery agents to avoid retention of siRNA within endosomes. Another common strategy is the modification of the nucleotides of siRNA, such as the replacement of the 2'-hydroxyl uridines with 2'-O-methyl uridines.

Careful design of siRNA is essential to prevent off-target effects. Nucleic acid-base pairing is highly specific, and mismatches at one or a small number of positions is often sufficient to completely prevent hybridization under physiological conditions. It is desirable therefore to synthesize more than one siRNA for each target to control for off-target effects.

Naked siRNA and shRNA Delivery to Tumor Cells In Vivo

RNA interference (RNAi) is a post-transcriptional gene silencing event in which short double-stranded RNA (siRNA) degrades target mRNA. Silencing oncogenes or other genes contributing to tumor progression by RNAi can be a therapeutic strategy for cancer. Delivery of RNAi effector to tumor cells is one of the key factors determining the efficacy, because the gene silencing is limited in cells reached by RNAi effector. In this study, we developed a tumor cell line stably expressing reporter genes to sensitively and quantitatively evaluate RNAi effect in tumor cells in vivo. Genetically labeled tumor cells were inoculated into the footpad or via the portal vein of mice to establish primary and metastatic tumor models, respectively. Intratumoral injection of either naked siRNA or naked short-hairpin RNA (shRNA)-expressing plasmid DNA followed by electroporation was effective in suppressing the expression of the target gene in tumor cells. Intravenous injection of naked RNAi effectors by the hydrodynamics-based procedure inhibited the gene expression in tumor cells colonizing in the liver. Then, shRNA-expressing plasmid DNA targeting β-catenin or hypoxia inducible factor-1α (HIF-1α) was delivered to tumor cells in order to inhibit tumor growth in vivo. In the primary tumor model, delivery of shRNA-expressing plasmid DNA targeting β-catenin or HIF-1α was effective in inhibiting tumor growth, whereas only shRNA-expressing pDNA targeting HIF-1α was effective in the hepatic metastasis model. We also found that HIF1 expression in liver cells is elevated by inoculation of tumor cells into the portal vein, and the silencing of the expression in normal liver cells is also effective in inhibiting tumor metastasis to the liver. Takahashi et al, (Grad. Sch. Pharm. Sci., Kyoto Univ.).

RNAi offers more specificity and flexibility than traditional drugs in treating diseases. When short pieces of double-stranded RNA (designed to target a particular gene) are introduced into cells, they are separated into single strands, with one binding to the target RNA and causing its demise. Thus the target RNA is no longer expressed.

Delivery as Particles or Complexes

Tekmira offers a delivery reagent designed to lengthen the time of the RNA therapeutic agent in the body, facilitating its uptake into distal target sites. Tekmira's technology, known as SNALP (stable nucleic acid-lipid particles), comprises lipid nanoparticles that encapsulate siRNA for delivery to specific disease sites. Tekmira develops agents in partnership with others, such as Alnylam and Roche, that use Tekmira's delivery technology in developing RNAi therapies. Alnylam recently received FDA clearance to begin clinical trials of ALN-VSP, an RNAi drug being developed for the treatment of liver cancer and cancer with liver involvement. ALN-VSP was developed using Tekmira's SNALP delivery technology and is scheduled to enter the clinic in the first half of 2009. Tekmira's ApoB SNALP for severe high cholesterol is expected to enter a phase 1 human clinical trial in 2009, and their anti-cancer PLK1 SNALP is also under development.

Intradigm combines siRNA molecules with their PolyTran™ peptide-based polymers to create nanoparticles for RNAi delivery. This technology can deliver RNA molecules to almost any body tissue. Intradigm modifies their nanoparticles according to the delivery challenges faced. By PEGylating its nanoparticles, Intradigm can increase half-life and tissue accumulation The therapeutic agent is targeted to particular tissues by attaching specific targeting moieties to the nanoparticles.

Once the RNAi agent has been delivered, the next significant challenge is getting it to the right place. Invitrogen's new RNAi delivery reagent, Invivofectamine™, facilitates systemic in vivo delivery and is non-toxic. It is especially effective when used together with their Stealth™ RNAi duplexes, which have been chemically modified so that only one strand participates in RNAi (reducing off-target effects), and the RNA evades the host immune response.

Invitrogen siRNAs Specific for ANXA9

ANXA9 Stealth™ Select RNAi HSS 112234 20 nM
ANXA9 Stealth™ Select RNAi Set of 3 3×20 nM
ANXA9 Stealth™ Select RNAi HSS112235 20 nM
ANXA9 Stealth™ Select RNAi HSS112236 20 nM MDRNA takes two approaches to design and delivery with their UsiRNA and meroduplex platforms. Their platform employs strategically placed non-nucleotide entities termed Unlocked Nucleobase Analogs (UNA) in addition to RNA to form a short double-stranded RNA-based oligonucleotide. UsiRNAs are protected from degradation and immune detection, and reduce off-target effects. Meroduplex is based on the concept that placing a nick or gap in the passenger strand will minimize off-target activity related to the passenger strand A nicked or gapped passenger strand biases the siRNA to load the guide strand into the RNAi machinery, thus maximizing the likelihood that the guide strand will appropriately silence the gene target.

In some cases a decision needs to made whether to use an siRNA or an shRNA. siRNA (21 nt) or an shRNA (50 mer) oligo, anneal them and put them into a siRNA vector. Synthetic siRNAs are easy to make, especially in applications for transient transfection. shRNAs take time to build, for stable transfection, tend to cause interferon response in vivo, but shRNAs are best to accomplish stable-knockdown of expression in the tumor cell in vivo.

For shRNAs, the procedure is to clone, verify insert, determine how much of the shRNA the target cells are expressing, and then preferably use viral vectors for delivery of shRNA. Nonviral vectors such as nanostructures, and microparticles also can be used.

The mechanism to which RNAi works in the cell is the same with shRNA and siRNA. Only the enzyme dicer will cleave the shRNA into an siRNA like oligo (removing the hairpin).The enzyme recognizes an oddly shaped hairpin structure and cleaves it.

Once dsRNA enters the cell, it is cleaved by an RNase III-like enzyme, Dicer, into double stranded small interfering RNAs (siRNA) 21-23 nucleotides in length that contain 2 nucleotide overhangs on the 3' ends (9-11). In an ATP dependent step, the siRNAs become integrated into a multi-subunit protein complex, commonly known as the RNAi induced silencing complex (RISC), which guides the siRNAs to the target RNA sequence. At some point the siRNA duplex unwinds, and it appears that the antisense strand remains bound to RISC and directs degradation of the complementary mRNA sequence by a combination of endo and exonucleases.

Using synthetic, short double-stranded RNAs that mimic the siRNAs produced by the enzyme dicer, sequence specific gene silencing is achieved in mammalian cells without inducing the interferon response.

shRNA Inhibition of ANXA9 Expression

Vorhies and Nemunaitis, 2009, Volume 480, *Macromolecular Drug Delivery* Humana Press 10.1007/978-1-59745-429, 2978-1-59745-429-2, use DNA vector-based short hairpin RNA (shRNA) as a means of effecting RNA interference (RNAi) for the precise disruption of gene expression to achieve a therapeutic effect. The clinical usage of shRNA therapeutics in cancer is limited by obstacles related to effective delivery into the nuclei of target cancer cells. Significant pre-clinical data have been amassed about biodegradable and non-biodegradable polymeric delivery vehicles that are relevant for shRNA delivery into humans. Some of the leading candidates for clinical usage have potential for usage in cancer shRNA therapeutics. Biodegradable and non-biodegradable delivery vehicles can be used.

An alternate to individual chemical synthesis of siRNA is to construct a sequence for insertion in an expression vector. Several companies offer RNAi vectors for the transcription of inserts. Some use an RNA polymerase III (Pol III) promoter to drive expression of both the sense and antisense strands separately, which then hybridize in vivo to make the siRNA. Other vectors are based on the use of Pol III to drive expression of short "hairpin" RNAs (shRNA), individual transcripts that adopt stem-loop structures, which are processed into siRNAs by the RNAi machinery. Typical shRNA design consists of two inverted repeats containing the sense and antisense target sequences separated by a loop sequence. Commonly used loop sequences contain 8-9 bases. A terminator sequence consisting of 5-6 poly dTs is present at the 3' end and cloning sequences can be added to the 5' ends of the complementary oligonucleotides.

Targeted Nanoparticles for Cancer Treatment

Targeted nanoparticles incorporating siRNA offer promise for cancer treatment. Use of targeted nanoparticles offers promising techniques for cancer treatment. By using targeted nanoparticles, researchers have demonstrated that systemically delivered siRNA can slow the growth of tumors in mice without eliciting the toxicities often associated with cancer therapies. NSTI Nanotech 2007. siRNA are incorporated into nanoparticles that are formed completely by self-assembly, using cyclodextrin-containing polycations. Dosing schedules and surface modifications on the efficacy of these siRNA nanoparticles is determined before a clinical trial.

Methods of Treatment

The ANXA9 inhibitor peptides and nucleic acids of the present invention, such as the siRNA or shRNA ANXA9 inhibitor, also can be used to treat or prevent a variety of disorders associated with reduced survival rate, especially as related to cancers. The peptides and nucleic acids are administered to a patient in an amount sufficient to elicit a therapeutic response in the patient (e.g., reduction of tumor size and growth rate, prolonged survival rate, reduction in concurrent cancer therapeutics administered to patient). An amount adequate to accomplish this is defined as "therapeutically effective dose or amount."

The peptides and nucleic acids of the invention can be administered directly to a mammalian subject using any route known in the art, including e.g., by injection (e.g., intravenous, intraperitoneal, subcutaneous, intramuscular, or intradermal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Administration of the peptides and nucleic acids of the invention can be in any convenient manner, e.g., by injection, intratumoral injection, intravenous and arterial stents (including eluting stents), catheter, oral administration, inhalation, transdermal application, or rectal administration. In some cases, the peptides and nucleic acids are formulated with a pharmaceutically acceptable carrier prior to administration. Pharmaceutically acceptable carriers are determined in part by the particular composition being administered (e.g., nucleic acid or polypeptide), as well as by the particular method used to administer the composition. Accordingly, there are a wide variety of suitable formulations of pharmaceutical compositions of the present invention (see, e.g., Remington's Pharmaceutical Sciences, $17^{th}$ ed., 1989).

The dose administered to a patient, in the context of the present invention should be sufficient to effect a beneficial therapeutic response in the patient over time. The dose will be determined by the efficacy of the particular vector (e.g. peptide or nucleic acid) employed and the condition of the patient, as well as the body weight or surface area of the patient to be treated. The size of the dose also will be determined by the existence, nature, and extent of any adverse side-effects that accompany the administration of a particular peptide or nucleic acid in a particular patient.

In determining the effective amount of the vector to be administered in the treatment or prophylaxis of diseases or disorder associated with the disease, the physician evaluates circulating plasma levels of the polypeptide or nucleic acid, polypeptide or nucleic acid toxicities, progression of the disease (e.g., breast cancer), and the production of antibodies that specifically bind to the peptide. Typically, the dose equivalent of a polypeptide is from about 0.1 to about 50 mg per kg, preferably from about 1 to about 25 mg per kg, most preferably from about 1 to about 20 mg per kg body weight. In general, the dose equivalent of a naked c acid is from about 1 µg to about 100 µg for a typical 70 kilogram patient, and doses of vectors which include a viral particle are calculated to yield an equivalent amount of therapeutic nucleic acid.

For administration, polypeptides and nucleic acids of the present invention can be administered at a rate determined by the LD-50 of the polypeptide or nucleic acid, and the side-effects of the polypeptide or nucleic acid at various concentrations, as applied to the mass and overall health of the patient. Administration can be accomplished via single or divided doses, e.g., doses administered on a regular basis (e.g., daily) for a period of time (e.g., 2, 3, 4, 5, 6, days or 1-3 weeks or more).

In certain circumstances it will be desirable to deliver the pharmaceutical compositions comprising the ANXA9 inhibitor peptides and nucleic acids disclosed herein parenterally, intravenously, intramuscularly, or even intraperitoneally as described in U.S. Pat. Nos. 5,543,158; 5,641,515 and 5,399,363. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

To date, most studies have been performed with siRNA formulated in sterile saline or phosphate buffered saline (PBS) that has ionic character similar to serum. There are minor differences in PBS compositions (with or without calcium, magnesium, etc.) and investigators should select a formulation best suited to the injection route and animal employed for the study. Lyophilized oligonucleotides and standard or siSTABLE siRNAs are readily soluble in aqueous solution and can be resuspended at concentrations as high as 2.0 mM. However, viscosity of the resultant solutions can sometimes affect the handling of such concentrated solutions.

While lipid formulations have been used extensively for cell culture experiments, the attributes for optimal uptake in cell culture do not match those useful in animals. The principle issue is that the cationic nature of the lipids used in cell culture leads to aggregation when used in animals and results in serum clearance and lung accumulation. Polyethylene glycol complexed-liposome formulations are currently under investigation for delivery of siRNA by several academic and industrial investigators, including Dharmacon, but typically require complex formulation knowledge. There are a few reports that cite limited success using lipid-mediated delivery of plasmids or oligonucleotides in animals.

Oligonucleotides can also be administered via bolus or continuous administration using an ALZET mini-pump (DURECT Corporation). Caution should be observed with bolus administration as studies of antisense oligonucleotides demonstrated certain dosing-related toxicities including hind limb paralysis and death when the molecules were given at high doses and rates of bolus administration. Studies with antisense and ribozymes have shown that the molecules distribute in a related manner whether the dosing is through intravenous (IV), subcutaneous (sub-Q), or intraperitoneal (IP) administration. For most published studies, dosing has been conducted by IV bolus administration through the tail vein. Less is known about the other methods of delivery, although they may be suitable for various studies. Any method of administration will require optimization to ensure optimal delivery and animal health.

For bolus injection, dosing can occur once or twice per day. The clearance of oligonucleotides appears to be biphasic and a fairly large amount of the initial dose is cleared from the urine in the first pass. Dosing should be conducted for a fairly long term, with a one to two week course of administration being preferred. This is somewhat dependent on the model being examined, but several metabolic disorder studies in rodents that have been conducted using antisense oligonucleotides have required this course of dosing to demonstrate clear target knockdown and anticipated outcomes.

Liposomes. In certain embodiments, the inventors contemplate the use of liposomes, nanocapsules, microparticles, microspheres, lipid particles, vesicles, and the like, for the administration of the ANXA9 inhibitory peptides and nucleic acids of the present invention. In particular, the compositions of the present invention may be formulated for delivery either encapsulated in a lipid particle, a liposome, a vesicle, a nanosphere, or a nanoparticle or the like. In one embodiment, the ANXA9 siRNA inhibitors (e.g., any one of SEQ ID NOS: 2-5) are entrapped in a liposome for delivery.

The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon & Papahadjopoulos, 1988; Allen and Choun, 1987; U.S. Pat. No. 5,741,516). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 m. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

Targeting is generally not a limitation in terms of the present invention. However, should specific targeting be desired, methods are available for this to be accomplished. For example, antibodies may be used to bind to the liposome surface and to direct the liposomes and its contents to particular cell types. Carbohydrate determinants (glycoprotein or glycolipid cell-surface components that play a role in cell-cell recognition, interaction and adhesion) may also be used as recognition sites as they have potential in directing liposomes to particular cell types.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 m) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684).

Gene Therapy. In certain embodiments, the nucleic acids encoding inhibitory ANXA9 peptides and nucleic acids of the present invention can be used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses an inhibitory ANXA9 peptides and nucleic acids of the present invention, thereby mitigating the effects of over amplification of a candidate gene associated with reduced survival rate.

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Feigner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

For delivery of nucleic acids, viral vectors may be used. Suitable vectors include, for example, herpes simplex virus vectors as described in Lilley et al., *Curr. Gene Ther.* 1(4): 339-58 (2001), alphavirus DNA and particle replicons as described in e.g., Polo et al., *Dev. Biol.* (Basel) 104:181-5 (2000), Epstein-Barr virus (EBV)-based plasmid vectors as described in, e.g., Mazda, *Curr. Gene Ther.* 2(3):379-92 (2002), EBV replicon vector systems as described in e.g., Otomo et al., *J. Gene Med.* 3(4):345-52 (2001), adeno-virus associated viruses from rhesus monkeys as described in e.g., Gao et al., *PNAS USA.* 99(18):11854 (2002), adenoviral and adeno-associated viral vectors as described in, e.g., Nicklin and Baker, *Curr. Gene Ther.* 2(3):273-93 (2002). Other suitable adeno-associated virus (AAV) vector systems can be readily constructed using techniques well known in the art (see, e.g., U.S. Pat. Nos. 5,173,414 and 5,139,941; PCT Publication Nos. WO 92/01070 and WO 93/03769; Lebkowski et al. (1988) *Mol. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol and Immunol.* 158: 97-129; Kotin (1994) *Human Gene Therapy* 5:793-801; Shelling and Smith (1994) *Gene Therapy* 1: 165-169; and Zhou et al. (1994) *J. Exp. Med.* 179:1867-1875). Additional suitable vectors include E1B gene-attenuated replicating adenoviruses described in, e.g., Kim et al., *Cancer Gene Ther.* 9(9):725-36 (2002) and nonreplicating adenovirus vectors described in e.g., Pascual et al., *J. Immunol.* 160(9):4465-72 (1998) Exemplary vectors can be constructed as disclosed by Okayama et al. (1983) *Mol. Cell. Biol.* 3:280.

Molecular conjugate vectors, such as the adenovirus chimeric vectors described in Michael et al. (1993) *J. Biol. Chem.* 268:6866-6869 and Wagner et al. (1992) *Proc. Natl. Acad. Sci. USA* 89:6099-6103, can also be used for gene delivery according to the methods of the invention.

In one illustrative embodiment, retroviruses provide a convenient and effective platform for gene delivery systems. A selected nucleotide sequence encoding an inhibitory ANXA9 nucleic acid or polypeptide can be inserted into a vector and packaged in retroviral particles using techniques known in the art. The recombinant virus can then be isolated and delivered to a subject. Suitable vectors include lentiviral vectors as described in e.g., Scherr and Eder, *Curr. Gene Ther.* 2(1):45-55 (2002). Additional illustrative retroviral systems have been described (e.g., U.S. Pat. No. 5,219,740; Miller and Rosman (1989) *BioTechniques* 7:980-990; Miller (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993) *Curr. Opin. Genet. Develop.* 3:102-109.

Other known viral-based delivery systems are described in, e.g., Fisher-Hoch et al. (1989) *Proc. Natl. Acad. Sci. USA* 86:317-321; Flexner et al. (1989) *Ann. N.Y. Acad. Sci.* 569: 86-103; Flexner et al. (1990) *Vaccine* 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al. (1993) *Circulation* 88:2838-2848; Guzman et al. (1993) *Cir. Res.* 73:1202-1207; and Lotze and Kost, *Cancer Gene Ther.* 9(8):692-9 (2002).

Combination Therapy.

In some embodiments, the inhibitory ANXA9 polypeptides and nucleic acids are administered in combination with a second therapeutic agent for treating or preventing cancer, including breast cancer. For example, an inhibitory ANXA9 siRNA of SEQ ID NO: 2-5 may be administered in conjunction with any of the standard treatments for breast cancer including, but not limited to, paclitaxel, cisplatin, carboplatin, chemotherapy, and radiation treatment.

The inhibitory ANXA9 polypeptides and nucleic acids and the second therapeutic agent may be administered simultaneously or sequentially. For example, the inhibitory ANXA9 polypeptides and nucleic acids may be administered first, followed by the second therapeutic agent. Alternatively, the second therapeutic agent may be administered first, followed by the inhibitory ANXA9 polypeptides and nucleic acids. In some cases, the inhibitory ANXA9 polypeptides and nucleic acids and the second therapeutic agent are administered in the same formulation. In other cases the inhibitory ANXA9 polypeptides and nucleic acids and the second therapeutic agent are administered in different formulations. When the inhibitory ANXA9 polypeptides and nucleic acids and the second therapeutic agent are administered in different formulations, their administration may be simultaneous or sequential.

In some cases, the inhibitory ANXA9 polypeptides and nucleic acids can be used to target therapeutic agents to cells and tissues expressing ANXA9 and other candidate genes that are related to reduced survival rate.

Kits

The present invention further provides kits for use within any of the above diagnostic methods. Such kits typically comprise two or more components necessary for performing a diagnostic assay. Components may be compounds, reagents, containers and/or equipment. For example, one container within a kit may contain an inhibitory ANXA9 polypeptides and nucleic acids. One or more additional containers may enclose elements, such as reagents or buffers, to be used in the assay. Such kits may also, or alternatively, contain a detection reagent as described above that contains a reporter group suitable for direct or indirect detection of antibody binding.

Kits can also be supplied for therapeutic uses. Thus, the subject composition of the present invention may be provided, usually in a lyophilized form, in a container. The inhibitory ANXA9 polypeptides and nucleic acids described herein are included in the kits with instructions for use, and optionally with buffers, stabilizers, biocides, and inert proteins. Generally, these optional materials will be present at less than about 5% by weight, based on the amount of polypeptide or nucleic acid, and will usually be present in a total amount of at least about 0.001% by weight, based on the polypeptide or nucleic acid concentration. It may be desirable to include an inert extender or excipient to dilute the active ingredients, where the excipient may be present in from about 1 to 99% weight of the total composition. The kits may further comprise a second therapeutic agent, e.g., paclitaxel, carboplatin, a chemotherapeutic agent.

EXAMPLES

Example 1

Inhibition of ANXA9 Induces Cell Apopotosis

It was found that silencing of ANXA9 inhibits breast cancer cell growth and cell proliferation and inhibition of ANXA9 expression in breast cancer cells induces cell apoptosis. Thus, ANXA9 is implicated in proliferative aspects of breast cancer pathophysiology and serves as a possible therapeutic target in breast cancer.

A comprehensive study of gene expression and copy number in primary breast cancers and breast cancer cell lines was carried out, whereby we identified a region of high level amplification on chromosome 1q21 that is associated with reduced survival duration. The annexin family member, ANXA9, identified herein, maps to the region of amplification at 1q21. siRNA knockdown was applied to explore how amplification and over-expression of this particular gene play a role in breast cancer pathophysiology and to determine if this gene may be a valuable therapeutic target.

We transiently transfected 83 nM of siRNA for ANXA9 into T47D, BT549, SUM52PE, 600MPE and MCF10A breast cancer cell lines. Non-specific siRNA served as a negative control. Cell viability/proliferation was evaluated by CellTiter-Glo® luminescent cell viability assay (CTG, Promega), cell apoptosis was assayed using YoPro-1 and Hoechst staining and cell cycle inhibition was assessed by measuring BrdU incorporation. All cellular measurements were made in adhered cells using the Cellomics high content scanning instrument. All assays were run at 3, 4, 5 and 6 days post transfection.

Briefly, the siRNA transfection protocol was as follows. Cells are plated and grown to 50-70% confluency and transfected using DharmaFECT1. In tubes, mix: Tube A: total volume 10 ul 9.5 uL SFM media+0.5 siRNA (varied according to the experiment design); Tube B: total volume 10 ul 9.8 uL SFM media+0.2 DharmaFECT1. Incubate tubes for 5 min. During this incubation, remove media from target cells and replace with SFM in each well. Add contents of Tube B to Tube A and mix gently. Incubate for 20 min at room temperature. Add 20 uL mixture solution dropwise to each well (final volume=100 uL). Leave for 4 h, aspirate off media and replace with full growth media and allow cells to grow for several days.

Cell growth analysis was carried out using the CellTiter-Glo® Luminescent Cell Viability Assay (Promega Cat #G7571/2/3). The luminescence signal of viable cells as measured the amount of ATP detected in the plates were read using a custom plate reader and program.

BrdU Staining and Fixation for Cellomics were used to measure cell proliferation and cell cycle analysis. To incorporate BrdU and fix the cells 10 uM final concentration of BrdU (Sigma #B5002) was added directly to cell media and pulsed for 30 minutes in tissue culture incubator. The media was removed and the cells washed 2× with 1× PBS and then 70% EtOH added to cover cells and fix for overnight at 4° C. Next day the 70% EtOH was removed and cells allowed to dry. Then 2N HCl was added and cells incubated at room temperature for 5-10 minutes, then removed and 1× PBS added to neutralize. Diluted anti-BrdU antibody (Mouse anti-BrdU Clone 3D4 (BD Pharmingen #555627)) 1:100 in 1× PBS/0.5% Tween-20. Anti-BrdU was added to cells (50 ul-96 well plate; 200 ul -24 well plate) and incubated for 45-60 minutes at room temperature on a rocker. Antibody was aspirated and cells washed 2× with 1× PBS/0.5% Tween-20. Rabbit Anti-mouse Alexa Fluor 488 (Invitrogen #A-11059) was diluted 1:250 in 1× PBS/0.5% Tween-20. Secondary antibody was added to cells and incubated 30-60 minutes at room temperature on a rocker then washed 3× with 1× PBS/0.5% Tween-20. After the last wash was removed and cells were incubated with 1 ug/ml Hoechst 33342 (Sigma #B2261) diluted in 1× PBS for 45 minutes at room temperature on a rocker. Cells were washed and covered with 1× PBS. Plates were scanned or stored at 4° C. for later scanning on Cellomics.

YoPro-1 Staining for Cellomics was used for cell apoptosis analysis. Add YoPro-1 (Final use at 1 ug/ml) and Hoechst (Final use at 10 ug/ml) directly to cell media. Place in 37° C. incubator for 30 min. Then read directly on Cellomics.

Significant knockdown of ANXA9 was achieved in BT549 and T47D cells transfected with siRNA-ANXA9 for 48 hr, 72 hr and 96 hr. Silencing of ANXA9 significantly reduced the proliferation of breast cancer cells and inhibited the BrdU incorporation after treatment with siRNA compared to controls. Knockdown of ANXA9 in breast cancer cells also induced significant levels of apoptosis. Furthermore, we found that cells had very good response when the concentration of siRNA-ANXA9 were higher than 30 nM. The current results suggested that silencing expression of ANXA9 is a novel approach for inhibition of breast cancer cell growth. ANXA9 may serve as a new candidate therapeutic target for treatment of breast cancer with poor outcome.

Example 2

Delivery Inhibitors of ANXA9

Inhibitory RNAs (iRNAs) such as siRNA and shRNA oligonucleotide inhibitors, and/or small molecular inhibitors can be developed targeting ANXA9 gene expression. To delivery these inhibitory molecules, formulations are first tested on cultured cells and xenografts, then animal models to normal cells, animal models to cancerous tumor cells, and final humans having cancerous tumors. There are several approaches to development of amplicon gene inhibitors for ANXA9. One approach will be to deliver optimized siRNAs complexed to polymer-coated cationic liposomes. The other approach will be to develop small molecule inhibitors for targets located in key amplified regions in breast tumors that have been functionally validated using siRNAs. Apoptotic indices will be measured for cell lines and xenografts in which the target genes are amplified and that respond apoptotically to treatment with siRNAs. Lipofectamine constructs that induce apoptosis in cell lines/xenografts are used where the target is amplified and not when the target is not amplified. Optimally, any inhibitor is minimally toxic to non-cancer cells in the human. Various concentrations of inhibitor will be tested to determine the effective and least toxic dose.

Liposome Bound siRNA Inhibitors

Optimized siRNAs (e.g., SEQ ID NOS: 2-5) directed against ANXA9 will be complexed to non-viral gene delivery system that can be administered in vivo or in vitro. Initially the gene target is ANXA9 (designated siANXA9) and its scrambled controls (designated siANXA9$^{sc}$). Specifically, siRNAs will be bound to SN (e.g. siANXA9-SN), a polymer-coated cationic liposome formulation composed of 1,2-di-palmitoyl-sn-glycerol-3-ethylphosphocholine, 1,2-dipalmi-toyl-sn-glycero-3-phosphoethanoamine-N-polyethyleneglycol-5000 and polyethylenimine. The siRNAs are entrapped in the liposome after the thin-lipid film is hydrated and extruded through a filter with 0.2 μm diameter pores. The lipid/siRNA ratio will be 12:1, and the liposomal siRNA particle size will be 70-170 nm in diameter. The extended polyethylene glycol (PEG) on the surface of the liposomes protects the liposome from being attacked by blood components and engulfed by phagocytes in vivo thereby increasing tumor specificity and increasing stability.

Small Molecule Inhibitors

Small molecule inhibitors will be developed in collaboration with other facilities having the required expertise. This work will begin with identification of lead compounds by setting up a high throughput screen, obtaining the necessary proteins and reagents to carry out the screen, and conducting the screen using a proprietary collection of small molecules. For those targets whose function is known, we set up functional assays. If the function of the protein target is previously unknown (e.g. ANXA9) or cannot be predicted from homology modeling, we use a binding assay that involves affinity selection with mass spectrometry. Once lead compounds have been identified in the high throughput screen, they will be tested in cell-based apoptosis assays using cells that have the region amplified where the target gene is located. These results will be compared to those obtained in apoptosis assays using cells that do not have the region amplified. Next, promising lead compounds will be optimized for binding to the target, cell penetration and cell-based activity, and pharmacokinetic properties. If a suitable optimized lead compound can be obtained, it will be tested in xenograft tumor models for efficacy and possible toxicity.

Test Systems

Inhibitors will be tested in cell lines that are amplified at the target loci as determined by array CGH. Cells in 24-well cultures will be treated with inhibitors over a concentration range in order to determine the degree to which target gene expression is reduced at the RNA level and the concentration that induces apoptosis at 90% of the maximum achieved (maximum apoptosis index, MAI). Three different target-amplified cell lines will be tested in order to determine an average working concentration for further experiments. Quantitative RT-PCR will be used to assess changes in gene expression.

Inhibitors will be tested in vivo in orthotopic xenograft models of breast cancer have proven useful for the characterization of breast tumor growth and metastasis in vivo as well as for testing novel therapeutics for the treatment of breast cancer (Stakleff, K. D. & Von Gruenigen, V. E. Rodent models for breast cancer research. *Int J Gynecol Cancer* 13, 405-13 (2003); Vanderhyden, B. C., Shaw, T. J. & Ethier, J. F. Animal models of breast cancer. *Reprod Biol Endocrinol* 1, 67 (2003); and Senterman, M. K., Dawson, K., Crane, C. A. & Vanderhyden, B. C. Characterization of intraperitoneal, orthotopic, and metastatic xenograft models of human breast cancer. *Mol Ther* 10, 1032-42 (2004). Xenografts will be established by injecting human breast cancer cell lines directly into the peritoneum of immunodeficient nude mice. This orthotopic model of breast cancer mimics the pattern of tumor spread in the peritoneum seen in the majority of human patients with advanced disease.

Not all xenografts of human breast cancer cell lines form intraperitoneal tumors. Fortunately, we have at least two breast cancer cell lines that express increased copy numbers of each of our target loci (1q21, 8q24, 11q13, and 20q11-q13) and that are also suitable for xenograft studies (Senterman, M. K., et al., *Mol Ther* 10, 1032-42 (2004); Hamilton, T. C. et al. Characterization of a xenograft model of human breast carcinoma which produces ascites and intraabdominal carcinomatosis in mice. *Cancer Res* 44, 5286-90 (1984); Buick, R. N., Pullano, R. & Trent, J. M. Comparative properties of five human breast adenocarcinoma cell lines. *Cancer Res* 45, 3668-76 (1985); Lau, D. H., Lewis, A. D., Ehsan, M. N. & Sikic, B. I. Multifactorial mechanisms associated with broad cross-resistance of breast carcinoma cells selected by cyanomorpholino doxorubicin. *Cancer Res* 51, 5181-7 (1991). OVCAR3 demonstrates amplification of all three loci. HEY will be used to generate xenografts to study amplification at 8q24 and 20q11-q13, and ES2 will be utilized to study amplification at 11q13. Multiple lies for each target is advantageous since individual cell lines demonstrate different histological and growth characteristics (Senterman, M. K., et al., (2004)). For example, data (not presented) demonstrate mice injected intraperitoneally (i.p.) with the breast cancer cell lines HEYA8 and SKOV3. Histological sections of these tumors demonstrate similarity to human tumors. In this experiment, 9 out of 10 mice injected with HEYA8 cells developed peritoneal tumors and all 10 mice injected with SKOV3 developed tumors. Mice receiving an i.p injection of HEYA8 cells (median survival 30 days, range 28-42 days) developed large (up to 10 mm in diameter) peritoneal lesions with 2-4 discrete lesions per mouse. Mice given an i.p injection of SKOV3 (median survival 40 days, range 35-51 days) developed multiple nodules ranging in size from 2-5 mm in diameter.

In another embodiment, we will select compounds that induce high levels of apoptosis in cell lines in which the target is amplified and low levels otherwise and that inhibit growth in xenografts where the target is amplified (e.g. HEY for ANXA9) and not in xenografts where the target is not amplified (e.g. SKOV3 for ANXA9). Apoptosis will be measured in vitro as described above. Apoptosis will be measured in xenografts by assessing the frequency of pyknotic nuclei in four high powered fields in H&E sections and/or by assessing the frequency of cells that stain positively with antibodies against caspase 3.

Activity

We will assess activity of candidate inhibitory formulations (e.g. siANXA9-DOPC) and control formulations (e.g. siANXA9$^{sc}$-DOPC) in mice bearing well established xenografts in which the target gene is amplified. Six groups of 10 mice will be injected i.p. with $10^6$ tumor cells (e.g. HEY for ANXA9). Tumors will be allowed to progress for 7 days at which time the animals will be injected with a single dose of each formulation as several different concentrations and three mice will sacrificed at 1 hour, 6 hours, 24 hours, 4 days, 7 days and 10 days. Each experiment will be repeated in triplicate. Samples of tumor tissue will be flash frozen for protein and RNA extraction, and formalin-fixed and paraffin-embedded for immunohistochemical analysis of target protein expression levels following siRNA therapy. An apoptotic index will be measured as the frequency of pyknotic nuclei in four high power fields in H&E sections and/or the frequency of cells that stain positively with an antibody against caspase 3. These studies will establish the 90% MAI concentration for each formulation. Inhibition of gene expression at the RNA level will be measured using quantitative RT-PCR. Inhibition at the protein level will be measured using western analysis and/or immunohistochemistry when suitable antibodies are available.

Successful development of inhibitory constructs that can be delivered in vivo builds on liposome mediated gene delivery technologies described above and on high throughput small molecule screening. Some problems with siRNAs may arise due to inefficient delivery or to unacceptable toxicity. These may be overcome, for example, by using neutral liposomes and/or by targeting the liposomes to the folate receptor (FR), to increase the specificity for breast cancer. FR is a glycosylphosphatidylinositol-anchored membrane protein and over expressed in a wide variety of human tumors while exhibiting highly restricted normal tissue distribution and the subtype, FR-α, is over expressed in 90% of breast carcinomas. These and other methods are more fully addressed herein.

Example 3

Effective Formulations of ANXA9 Inhibitors

ANXA9 (and other) inhibitory formulations developed will be tested for their preferential effectiveness against xenografts that are amplified at the target loci and to test whether they enhance response to platinum and taxane compounds. The most effective formulation will be developed for clinical application. Basically we will establish xenograft models that are positive (i.e. amplified at least log 2>0.5) for each amplified locus; determine baseline paclitaxel and carboplatin responses for all xenograft models; determine responses to an anti ANXA9 Rx; measure responses to next priority target (designated T2) and responses to ANXA9 plus carboplatin; and finally measure responses to ANXA9+paclitaxel and responses of T2+carboplatin Formulations that inhibit gene expression in xenografts and for which the 90% MAI concentration is less than the LD50 in xenografts that are amplified at the target locus will be tested at the 90% MAI concentration in xenografts in which the target locus is not amplified.

Formulations that exhibit target specificity (i.e. induce apoptosis in models in which the target is amplified and not in models where the target is not amplified) will be tested against xenografts in which the target is amplified at the 90% MAI concentration and at 2- and 4-fold lower doses in combination with carboplatin or paclitaxel (given at the MTD) in order to determine the extent to which amplicon inhibitors can enhance sensitivity to platinum/taxane based therapies. OVCAR3, HEY and ES2 will be used in these studies since each target locus is amplified in two or more of these lines, all form xenografts and all demonstrate some resistance to cis-platinum. Assuming that successful inhibition of a target gene and an apoptotic response can be achieved in vivo, we will evaluate inhibitor treatment schedules alone and in combination with carboplatin or paclitaxel.

We will assess the target specificity of targeted formulations by treating mice bearing well established xenografts that are not amplified for at the target will be injected with a single dose of the inhibitory formulation. As an example, mice bearing well established ES2 xenografts (not amplified for ANXA9) will be treated with siANXA9-DOPC and assessed for apoptotic response. Mice will be sacrificed at 1 hour, 6 hours, 24 hours, 4 days, 7 days and 10 days. The experiment will be repeated in triplicate. Samples of tumor tissue will be flash frozen for protein extraction, and formalin-fixed and paraffin-embedded for immunohistochemical analysis of apoptotic response. Lack of apoptotic response will be taken as an indication of specificity since all formulations tested at this stage will already have demonstrated effectiveness in xenografts in which the target is amplified.

We will evaluate the efficacy of inhibitory gene-targeted formulations (e.g. siANXA9-DOPC) against tumors amplified at the target locus alone and in combination with carboplatin (60 mg/kg twice weekly) and paclitaxel (100 μg/week). Six groups of ten mice will be injected intraperitoneally with $10^6$ cells from a line in which the target is amplified (e.g. HEY for ANXA9). Tumors will be allowed to progress for 7 days at which time the animals will be divided into six treatment groups; untreated; carboplatin iv twice weekly; paclitaxel iv weekly; gene targeted formulation iv twice weekly; gene targeted formulation plus carboplatin twice weekly; and gene targeted formulation plus paclitaxel weekly. Treatment will be conducted for four weeks, at which time the animals will be sacrificed and a necropsy performed. All tumor tissue will be excised from each mouse and weighed. Total tumor weight will be compared between treatment groups. In addition, tumors will be formalin-fixed and paraffin embedded for the comparison and analysis of histological changes resulting from each therapeutic regime.

Outcomes to be observed include gene amplification/expression levels and apoptotic response in vitro and tumor growth and survival in vivo. Survival data will be analyzed using Kaplan-Meier estimates and compared using the log-rank test. Continuous outcomes will be compared across treatment groups using ANOVA. Continuous measures will be compared against each other (e.g. amplification versus apoptosis) using regression analysis. Tumor growth data will be analyzed using repeated measures ANOVA. We will compute appropriate sample sizes for all animal experiments. For example, based on previous experiments we know that the standard deviation of weights in normal control mice is generally less than 10% of the mean body weight. If a difference of 15% between control and treatment groups is of scientific interest and assuming body weights are normally distributed, then to achieve a 90% power to detect a 15% difference in weight between two groups using a two-sided test at a significance level of 10% requires 11 animals per group.

Example 4

In Vivo siRNA Delivery

The feasibility of therapeutic liposomal siRNA delivery to tumors in vivo has been demonstrated herein. The results of the studies are described below. This technology will be adapted to inhibit ANXA9 and other amplicon genes in preclinical mouse xenograft models of breast cancer.

Liposome Formulation

Gene specific siRNAs, and corresponding scrambled controls, were encapsulated in 1,2-Dioleoyi-sn-glycero-3-phosphatidylcholine (DOPC). DOPC and siRNA were mixed in the presence of excess tertiary-butanol at a ratio of 1:10 siRNA:DOPC (weight:weight). Tween-20 was added to the mixture in a ratio of 1:19 Tween-20:siRNA/DOPC The mixture was vortexed, frozen in an acetone/dry ice bath, and lyophilized. Prior to in vivo administration, this preparation was hydrated with normal saline at a concentration of 15 μg/ml, to achieve the desired dose in 150-200 μl per injection.

DOPC Liposomal Delivery of siRNA In Vivo

Studies were conducted that examined the kinetics, efficiency and distribution of siRNA delivery to both normal and tumor tissues in a mouse xenograft model of breast cancer using nanoparticle encapsulated as well as unmodified siRNA (Landen, C. N. et al. Therapeutic EphA2 gene targeting by in vivo liposomal siRNA delivery. *Nature Medicine* (2005)). Five micrograms of fluorescently labeled (Alexa-555), non-specific siRNA encapsulated in neutral liposomes (1,2-Dioleoyl-sn-glycero-3-phosphatidylcholine or DOPC) or unmodified Alexa-555-siRNA, was administered to mice intravenously with HEYA8 tumors (15 days following imp. injection of tumor cells). The delivery of Alexa-555-labeled siRNA to major organs, including heart, lung, brain, liver, kidney and spleen, as well as the tumor was analyzed using confocal microscopy. Interestingly, fluorescently labeled siRNA was detectable in tumor tissue as early as 1 hour following iv injection and persisted for up to 10 days (data not shown). This preferential uptake of long circulating liposomes and other macromolecules by tumors has been previously described as the enhanced permeability and retention (EPR) effect (Maeda, H., Wu, J., Sawa, T., Matsumura, Y. & Hori, K. Tumor vascular permeability and the EPR effect in macromolecular therapeutics: a review. *J Control Release* 65, 271-84 (2000)). Alexa-555-labeled siRNA accumulation was also detectable in normal liver, kidney, spleen and lung. Overall, uptake of DOPC encapsulated siRNA was 30-fold higher than that observed with unencapsulated siRNA. Furthermore, the neutral liposomal formulation of DOPC mediated siRNA delivery was 10-fold more efficient than that observed with a cationic DOTAP (N-[1-(2,3-Dioleoyloxy)propyl]-N,N,N-trimethylammonium methyl sulfate) liposome formulation. These data confirm increased efficiency of siRNA delivery using DOPC liposomes, and underscore the systemic delivery of siRNAs using this method.

Gene Specific Targeting of EPHA2 using DOPC-EPHA2 siRNA

Using this formulation of liposomal siRNA delivery, the in vivo inhibition of the EPHA2 receptor tyrosine kinase expression in breast tumors was subsequently demonstrated (Landen, C. N. et al. Therapeutic EphA2 gene targeting by in vivo liposomal siRNA delivery. *Nature Medicine* (Submitted) (2005)). EPHA2 is thought to play a role in the regulation of normal epithelial cell growth and migration. It is over expressed by a wide variety of epithelial tumors, and ectopic over expression of EPHA2 in normal cells is transforming (Walker-Daniels, J., Hess, A. R., Hendrix, M. J. & Kinch, M. S. Differential regulation of EphA2 in normal and malignant cells. *Am J Pathol* 162, 1037-42 (2003); Kinch, M. S. & Carles-Kinch, K. Over expression and functional alterations of the EphA2 tyrosine kinase in cancer. *Clin Exp Metastasis* 20, 59-68 (2003)), and represents a potential therapeutic target for the treatment of epithelial cancers. In agreement with these data, studies conducted by Thaker et al, demonstrated that EPHA2 protein levels are elevated in up to 75% of breast tumors and that EPHA2 over expression correlates with an aggressive phenotype and poor outcome (Thaker, P. H. et al. EphA2 expression is associated with aggressive features in breast carcinoma. *Clin Cancer Res* 10, 5145-50 (2004)).

EPHA2 is highly expressed in the HEYA8 and SKOV3ip1 cell lines. A single dose DOPC-encapsulated EPHA2 siRNA was administered to mice possessing HEYA8 cell tumors. Mice were sacrificed at 2, 4, 7 and 10 days following treatment. Western blot analysis was used to assess EPHA2 levels in tumors of DOPC-EPHA2 siRNA-treated mice as compared to mice treated with non-specific siRNA. EPHA2 was specifically down regulated in the tumors of DOPC-EPHA2 siRNA-treated mice. EPHA2 levels remained suppressed four days following treatment, but increased to normal levels by 10 days. Based on these results, it was determined that twice weekly administration of DOPC-EPHA2 siRNA should be sufficient to maintain EPHA2 inhibition in vivo.

Figure 8:
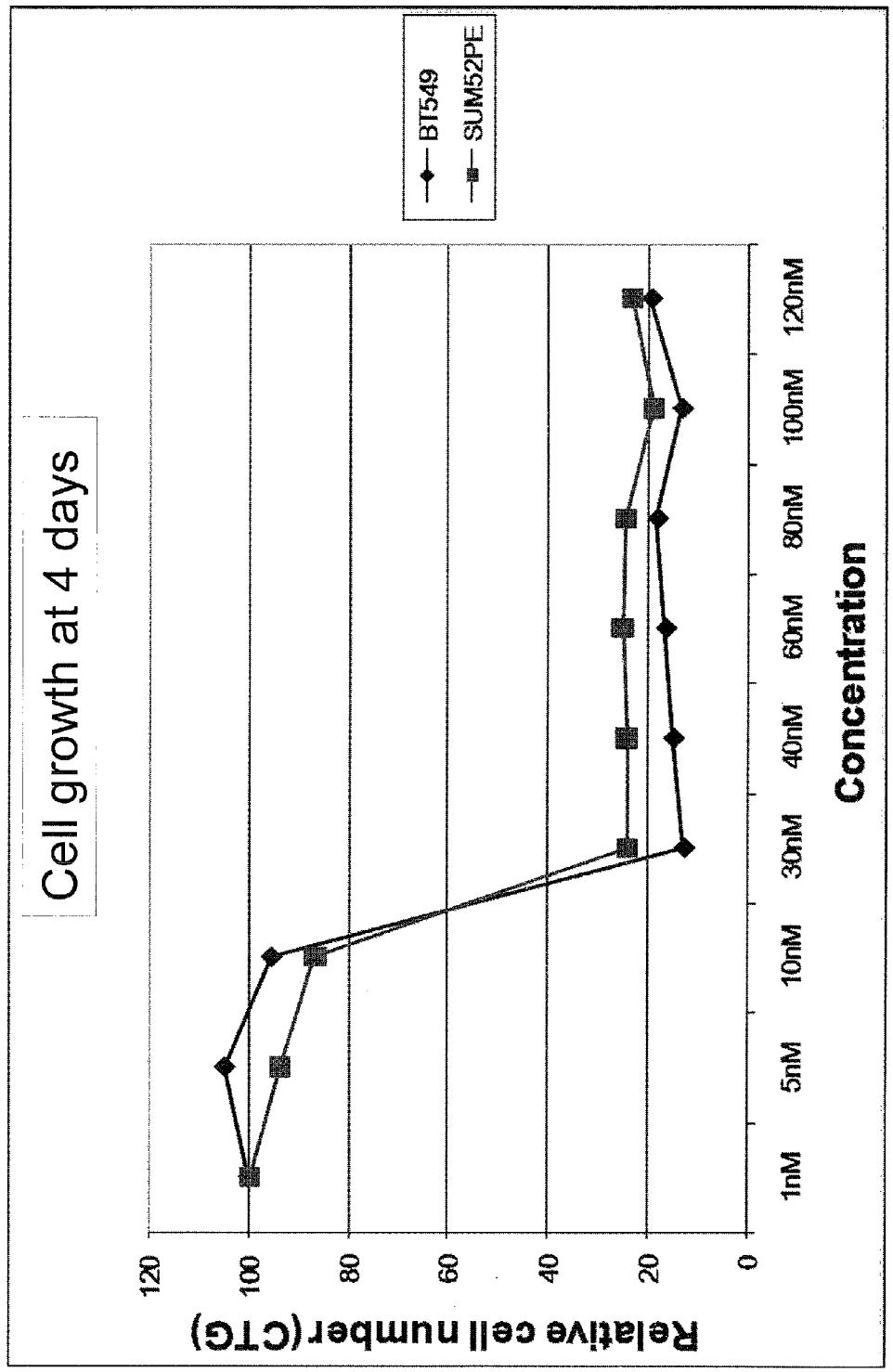
FIG. 8 is a graph showing that treating cells with a dosage higher than 30 nM of siRNA, the cell growth of BT549 and SUM52PE was significantly inhibited
Figure 9:
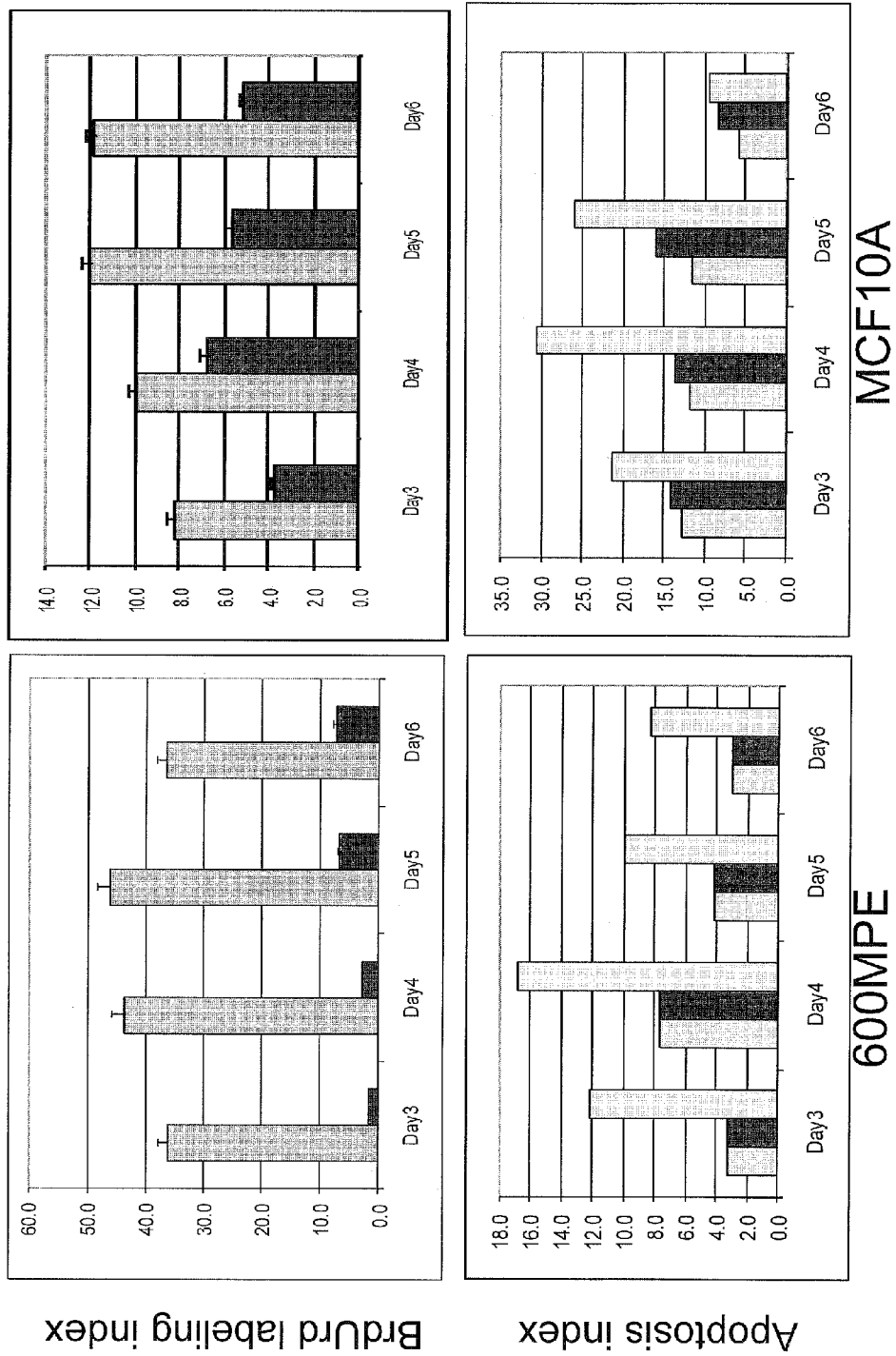
FIG. 9 is a panel of bar graphs which show siRNA inhibition of ANXA9 decreased proliferation and increased apoptosis. We measured the cell proliferation with BrdU and Hoechst staining using high throughput scanning. The % of BrdU staining was reduced in 600MPE cells when ANXA9 as knocked down compared to control cells. Yopro-1 and Hoechst staining to analyze the apoptotic cells. We can see the apoptosis rate was increased after cells treated with siANXA9 for 3 and 4 days. So the silencing of ANXA9 can inhibit cell proliferation and induce cell apoptosis.
Figure 10:
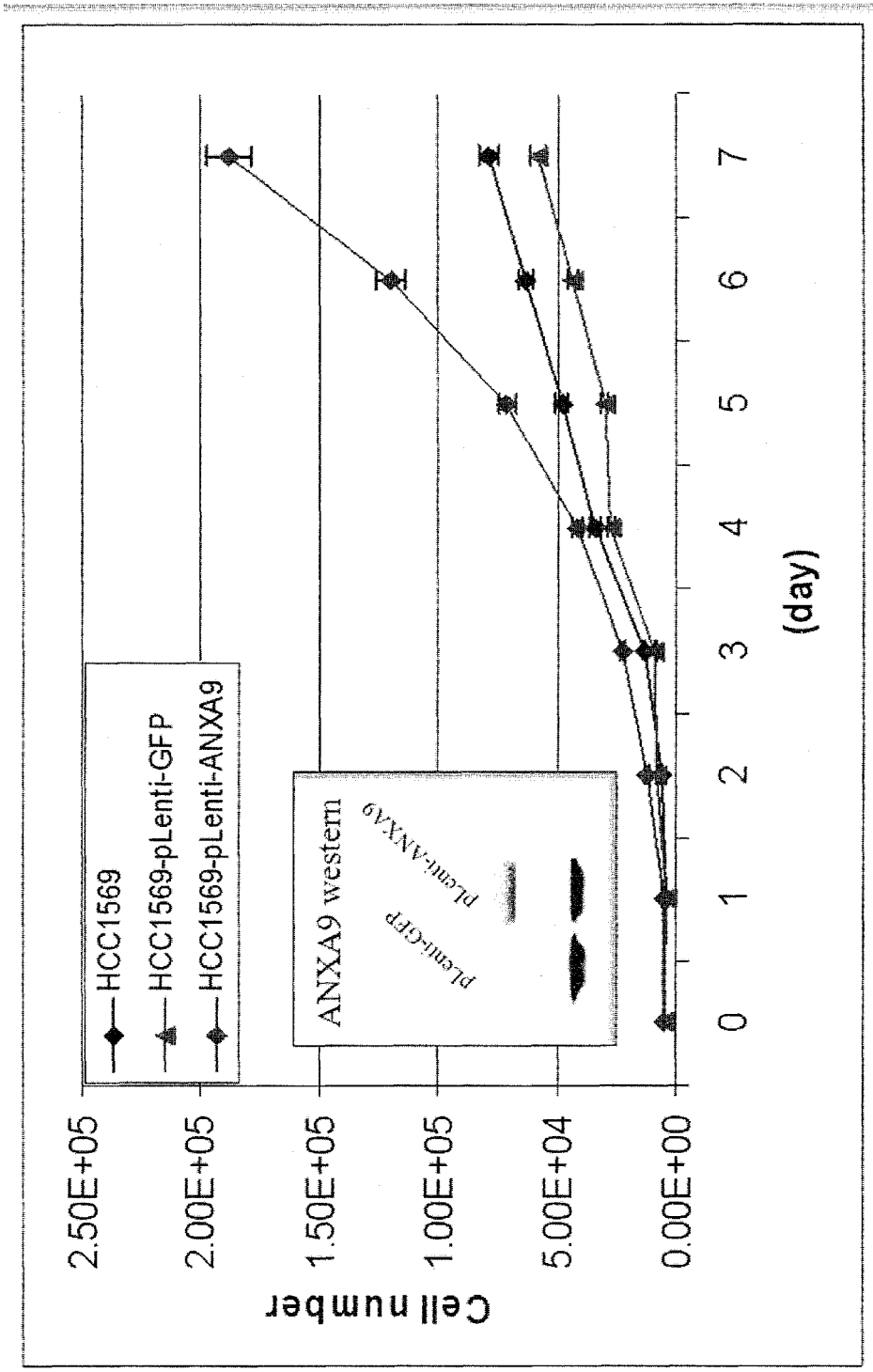
FIG. 10 is a graph showing that HCC1569 cells cloned to express ANXA9 exhibit increased cell growth when ANXA9 is over expressed compared to the GFP control cells.

For therapeutic studies, mice were injected with HEYA8 or SKOV3ip1 cells. One week later, mice were treated twice weekly with DOPC-EPHA2 siRNA (150 µg/kg) alone or in combination with weekly paclitaxel (100 µg), for four consecutive weeks. Treatment with DOPC-EPHA2 siRNA, paclitaxel and a combination of DOPC-EPHA2 siRNA and paclitaxel were all effective in reducing tumor size. Combination therapy was the most effective, leading to an 86-91% reduction in tumor size as compared to animal treated with control siRNA alone (FIG. 8).

Taken together, these data demonstrate that DOPC-siRNA gene silencing can be used to specifically down regulate protein expression in breast tumors in vivo, and represents a promising therapeutic for the treatment of breast cancer. The same or similar technology is capable of adaptation to target candidate genes such as ANXA9 which are amplified.

Example 6

Making siRNA Oligonucleotides for ANXA9 and Cell Transfection

Synthetic siRNAs against genes on 1q21 amplicon as well as negative control siRNA are obtained from Dharmacon Inc. One day before transfection, the cells are seeded at 3000-5000 per well in 96-well plates. For the transfection, 0.25 µL siRNA (20 µM stock) is mixed with 9.75 µL of Opti-MEM medium. After addition of mixture with 0.2 µL Dharmafect1 transfection reagent (Dharmacon) and 9.8 µL Opti-MEM medium, the mixture is incubated at room temperature for 20 min and subsequently added to cells. The final concentration of siRNA is 50 nM. After transfection with siRNAs for 72 hours, cells undergo a cell viability, proliferation and apoptosis assay.

Cell viability (growth) assay: The CellTiter-Glo® Luminescent Cell Viability Assay (Promega) provides a homogeneous bioluminescent assay designed for cytotoxicity and cell proliferation studies to determine. This assay is easily used to determine the number of viable cells present after various treatments. The manufacturer's protocol is used.

Apoptosis analysis: Cells are transfected with siRNAs. Apoptosis rate is assessed by automatic imaging analysis system Cellomics Arrayscan using YoPro-1(Invitrogen) and Hoechst33342(Sigma) dyes staining.

On top 3D culture: According to Reference (Lee et al., Nature Method, 2007 April;4(4):359-65.), three dimensional on-top cultures are prepared by trypsinization of cells from tissue culture plastic dishes, seeding of single cells on top of a thin gel of Matrigel (BD Biosciences), and addition of medium containing 5% matrigel. Culture for 4 days and then change medium every 2 days.

References for Enabling Various Cited Technologies and Procedures

Albertson, D. G., et al (2003). Chromosome aberrations in solid tumors. Nature Genetics 34: 369-376. Knuutila, S., Autio, K., and Aalto, Y. (2000). Online access to CGH data of DNA sequence copy number changes. Am J Pathol 157, 689. Baylin, S. B., and Herman, J. G. (2000). DNA hypermethylation in tumorigenesis: epigenetics joins genetics. Trends Genet 16, 168-174. Jones, P. A. (2005) Semin Hematol 42, S3-8. Overview of cancer epigenetics. Hanahan, D., and Weinberg, R. A. (2000). The hallmarks of cancer. Cell 100, 57-70. Perou, C. M., et al. (1999). Distinctive gene expression patterns in human mammary epithelial cells and breast cancers. Proc Natl Acad Sci USA 96, 9212-9217. Perou, C. M., et al. (2000). Molecular portraits of human breast tumors. Nature 406, 747-752. Sorlie, T., et al. (2001). Gene expression patterns of breast carcinomas distinguish tumor subclasses with clinical implications. Proc Nati Acad Sci USA 98, 10869-10874. Sorlie, T., et al. (2003). Repeated observation of breast tumor subtypes in independent gene expression data sets. Proc Nati Acad Sci USA 100, 8418-8423. Ramaswamy, S., et al. (2003). A molecular signature of metastasis in primary solid tumors. Nat Genet 33, 49-54. Esteva, F. J., et al (2005). Prognostic role of a multigene reverse transcriptase-PCR assay in patients with node-negative breast cancer not receiving adjuvant systemic therapy. Clin Cancer Res 11, 3315-3319. Gianni, L., et al. (2005). Gene Expression Profiles in Paraffin-Embedded Core Biopsy Tissue Predict Response to Chemotherapy in Women With Locally Advanced Breast Cancer. J Clin Oncol. van't Veer, L. J., et al. (2002). Gene expression profiling predicts clinical outcome of breast cancer. Nature 415, 530-536. Al-Kuraya, K., et al. (2004). Prognostic relevance of gene amplifications and co-amplifications in breast cancer. Cancer Res 64, 8534-8540. Kallioniemi, A., et al (1994). Detection and mapping of amplified DNA sequences in breast cancer by comparative genomic hybridization. Proc Natl Acad Sci USA 91, 2156-2160. Kallioniemi, O. P., et al (1992). ERBB2 amplification in breast cancer analyzed by fluorescence in situ hybridization. Proc Natl Acad Sci USA 89, 5321-5325. Press, M. F., et al. (2005). Diagnostic evaluation of HER-2 as a molecular target: an assessment of accuracy and reproducibility of laboratory testing in large, prospective, randomized clinical trials. Clin Cancer Res 11, 6598-6607. Tanner, M. M., et al. (1994). Increased copy number at 20q13 in breast cancer: defining the critical region and exclusion of candidate genes. Cancer Res 54, 4257-4260. Loo, L. W., et al. (2004). Array comparative genomic hybridization analysis of genomic alterations in breast cancer subtypes. Cancer Res 64, 8541-8549. Naylor, T. L., et al (2005). High resolution genomic analysis of sporadic breast cancer using array-based comparative genomic hybridization. Breast Cancer Res 7, R1186-1198. Pollack, J. R., et al. (1999). Genome-wide analysis of DNA copy-number changes using cDNA microarrays. Nat Genet 23, 41-46. Pollack, J. R., et al. (2002). Microarray analysis reveals a major direct role of DNA copy number alteration in the transcriptional program of human breast tumors. Proc Natl Acad Sci USA 99, 12963-12968. Volik, S., et al. (2003). End Sequence Profiling: sequence-based analysis of aberrant genomes. PNAS 100:7696-701. Anand N, et al. (2002) Protein elongation factor EEF1A2 is a putative oncogene in breast cancer. Nat Genet. 31:301-305. Gray, J. W., et al. (2003). Specific Keynote: Genome Copy Number Abnormalities in Breast Cancer. Gynecologic Oncology, Vol. 88, Issue 1, S16-S21. Cheng, K. W., et al. (2004) The RAB25 small GTPase determines aggressiveness of breast and breast cancers. Nat. Med. 10:1251-11256. Lapuk, A., et al. (2004). Computational BAC clone contig assembly for comprehensive genome analysis. Genes Chromosomes & Cancer 40:66-71. Isola, J. J., et al. (1995). Genetic aberrations detected by comparative genomic hybridization predict outcome in node-negative breast cancer. Am J Pathol 147, 905-911. Jain, A. N., et al. (2001). Quantitative analysis of chromosomal CGH in human breast tumors associates copy number abnormalities with p53 status and patient survival. Proc Natl Acad Sci USA 98, 7952-7957. Barlund, M., et al. (2000). Multiple genes at 17q23 undergo amplification and over expression in breast cancer. Cancer Res 60, 5340-5344. Ray, M. E. et al. (2004). Genomic and expression analysis of the 8p11-12 amplicon in human breast cancer cell lines. Cancer Res 64, 40-47. Yi, Y., et al. (2005). Coupled analysis of gene expression and chromosomal location. Genomics 85, 401-412. Kauraniemi, P., et al. (2001). New amplified and highly expressed genes discovered in the ERBB2 amplicon in breast cancer by cDNA microarrays. Cancer Res 61, 8235-8240. Kauraniemi, P. et al. (2003). Amplification of a 280-kilobase core region at the ERBB2 locus leads to activation of two hypothetical proteins in breast cancer. Am J Pathol 163, 1979-1984. Gelsi-Boyer, V., et al. (2005). Comprehensive profiling of 8p11-12 amplification in breast cancer. Mol Cancer Res 3, 655-667.

It is to be understood that this invention is not limited to particular embodiments described as the overarching use of the invention is applicable to a wide variety of embodiments. The terminology used is not intended to be limiting to the claims per se, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described in this specification.

The singular forms "a", "and", and "the" include plural referents unless the context clearly dictates otherwise. Thus, for example, reference to "nucleotide" includes more than on of that nucleotide, several nucleotides, and also a plurality of such nucleotides, While the present sequence, compositions and processes have been described with reference to specific details of certain exemplary embodiments thereof, it is not intended that such details be regarded as limitations upon the scope of the invention. The present examples, methods, procedures, specific compounds and molecules are meant to exemplify and illustrate the invention and should in no way be seen as limiting the scope of the invention.

Any patents, publications, publicly available sequences mentioned in this specification are indicative of levels of those skilled in the art to which the invention pertains and are hereby incorporated by reference to the same extent as if each was specifically and individually incorporated by reference. All publications mentioned herein are incorporated by reference to disclose and describe the methods and/or materials in connection with which the publications are cited.

What is claimed is:

1. A method of treating a breast cancer patient comprising the steps of:
   obtaining a breast cancer biopsy sample from the patient;
   detecting elevated expression of an ANXA9 gene in a tumor cell in the sample of said patient, whereby detection of elevated ANXA9 gene expression predicting poor prognosis for survival, and wherein said ANXA gene comprising the sequence of SEQ ID NO:1 and elevated ANXA9 gene expression is detected by detecting an isolated polynucleotide comprising the sequence of SEQ ID NO:1; and
   administering to the patient an effective amount of a therapeutic composition comprising an inhibitor of ANXA9 gene expression or ANXA9 protein function, wherein the therapeutic composition being administered inhibits expression of SEQ ID NO:1 or an expression product of SEQ ID NO:1 and wherein the therapeutic composition is an siRNA oligonucleotide inhibitor.

2. The method of claim 1 further comprising: detecting elevated ANXA9 gene expression comprising detecting amplification of the ANXA9 gene at locus 1q21 of a human chromosome wherein said elevated expression is as compared to a reference, wherein said ANXA9 gene comprising the sequence of SEQ ID NO: 1.

3. The method of claim 2, wherein the siRNA oligonucleotide inhibitor inhibits ANXA9 gene expression upon administration to a breast cancer tumor cell in the patient.

4. The method of claim 1 wherein said detecting elevated ANXA9 gene expression is detected by measuring amplification levels of SEQ ID NO: 1 or protein levels of the product of SEQ ID NO:1 as compared to a reference level.

5. The method of claim 4, wherein said detecting elevated ANXA9 gene expression is carried out by using fluorescent in situ hybridization, quantitative PCR, or immunochemical assays.

* * * * *

```
                        SEQUENCE LISTING

<160> NUMBER OF SEQ ID NOS: 5

<210> SEQ ID NO 1
<211> LENGTH: 1843
<212> TYPE: DNA
<213> ORGANISM: Homo Sapiens

<400> SEQUENCE: 1
acctggaccc acagggaagg cagtgcataa aagcctcctg tgtttgaggc tgagccgctg      60
agaggctgag tggagttcac tcacatggat tgaggcccag ttcctgggag aagagatgct     120
gggcaggaag gtgtctgcat gtgggactct gtacagcccg gtcctctccc acgtctggga     180
ggggccagag tcagacaact gctgggttcg tccctaagag aggtcatctg actggctgtt     240
cagcctaggc tgcacacacc cccactttcc tctaccaggc cacaccggag gcagtgctca     300
cacaggcaag ctaccaggcc acaacaacga cacccacctc acctctggca cctctgagca     360
tccacgtact tgcaagaact cttgctcaca tcagctaaga gattgcacct gctgacctag     420
agattccggc ctgtgctcct gtgctgctga gcagggcaac cagtagcacc atgtctgtga     480
ctggcgggaa gatggcaccg tccctcaccc aggagatcct cagccacctg ggcctggcca     540
gcaagactgc agcgtggggg accctgggca ccctcaggac cttcttgaac ttcagcgtgg     600
acaaggatgc gcagaggcta ctgagggcca ttactggcca aggcgtggac cgcagtgcca     660
ttgtggacgt gctgaccaac cggagcagag agcaaaggca gctcatctca cgaaacttcc     720
aggagcgcac ccaacaggac ctgatgaagt ctctacaggc agcactttcc ggcaacctgg     780
agaggattgt gatggctctg ctgcagccca cagcccagtt tgacgcccag gaattgagga     840
cagctctgaa ggcctcagat tctgctgtgg acgtggccat tgaaattctt gccactcgaa     900
ccccacccca gctgcaggag tgcctggcag tctacaaaca caatttccag gtggaggctg     960
```

```
tggatgacat cacatctgag accagtggca tcttgcagga cctgctgttg gccctggcca    1020 agggggccg tgacagctac tctggaatca ttgactataa tctggcagaa caagatgtcc    1080
aggcactgca gcgggcagaa ggacctagca gagaggaaac atgggtccca gtcttcaccc    1140
agcgaaatcc tgaacacctc atccgagtgt tgatcagta ccagcggagc actgggcaag    1200
agctggagga ggctgtccag aaccgttttcc atggagatgc tcaggtggct ctgctcggcc    1260
tagcttcggt gatcaagaac acaccgctgt actttgctga caaacttcat caagccctcc    1320
aggaaactga gcccaattac caagtcctga ttcgcatcct tatctctcga tgtgagactg    1380
accttctgag tatcagagct gagttcagga agaaatttgg gaagtccctc tactcttctc    1440
tccaggatgc agtgaaaggg gattgccagt cagccctcct ggccttgtgc agggctgaag    1500
acatgtgaga cttccctgcc ccaccccaca tgacatccga ggatctgaga tttccgtgtt    1560
tggctgaacc tgggagacca gctgggcctc caagtaggat aacccctcac tgagcaccac    1620
attctctagc ttcttgttga ggctggaact gtttctttaa aatcccttaa ttttcccatc    1680
tcaaaattat atctgtacct gggtcatcca gctccttctt gggtgtgggg aaatgagttt    1740
tctttgatag tttctgcctc actcatccct cctgtaccct ggccagaaca tctcactgat    1800
actcgaattc ttttggcaaa cttcaaaaaa aaaaaaaaaa aaa                      1843
```

```
<210> SEQ ID NO 2
<211> LENGTH: 21
<212> TYPE: RNA
<213> ORGANISM: Artificial Sequence
<220> FEATURE:
<223> OTHER INFORMATION: ANXA9 siRNA 1 sequence

<400> SEQUENCE: 2
aauuucaaug gccacguccu u                                              21

<210> SEQ ID NO 3
<211> LENGTH: 21
<212> TYPE: RNA
<213> ORGANISM: Artificial sequence
<220> FEATURE:
<223> OTHER INFORMATION: ANXA9 siRNA 2 sequence

<400> SEQUENCE: 3
auacucagaa ggucagucuu u                                              21

<210> SEQ ID NO 4
<211> LENGTH: 21
<212> TYPE: RNA
<213> ORGANISM: Artificial Sequence
<220> FEATURE:
<223> OTHER INFORMATION: ANXA9 siRNA 3 sequence

<400> SEQUENCE: 4
caugucuuca gcccugcacu u                                              21

<210> SEQ ID NO 5
<211> LENGTH: 21
<212> TYPE: RNA
<213> ORGANISM: Artificial Sequence
<220> FEATURE:
<223> OTHER INFORMATION: ANXA9 siRNA 4 sequence

<400> SEQUENCE: 5
uuccagagua gcugucacgu u                                              21
```